(12) United States Patent
Hercouet et al.

(10) Patent No.: US 7,429,275 B2
(45) Date of Patent: Sep. 30, 2008

(54) USE OF AT LEAST ONE COMPOUND CHOSEN FROM PORPHYRIN COMPOUNDS AND PHTHALOCYANIN COMPOUNDS FOR DYEING HUMAN KERATIN MATERIALS, COMPOSITIONS COMPRISING THEM, A DYEING PROCESS, AND COMPOUNDS THEREFOR

(75) Inventors: Leila Hercouet, Neuilly Plaisance (FR);
Alain Lagrange, Coupvray (FR)

(73) Assignee: L'Oreal S.A., Paris (FR)

( * ) Notice: Subject to any disclaimer, the term of this patent is extended or adjusted under 35 U.S.C. 154(b) by 174 days.

(21) Appl. No.: 11/315,281

(22) Filed: Dec. 23, 2005

(65) Prior Publication Data

US 2006/0156479 A1    Jul. 20, 2006

Related U.S. Application Data

(60) Provisional application No. 60/681,459, filed on May 17, 2005.

(30) Foreign Application Priority Data

Dec. 23, 2004    (FR) .................................. 04 53219

(51) Int. Cl.
*A61Q 5/10* (2006.01)
*C07B 47/00* (2006.01)

(52) U.S. Cl. ....................... 8/405; 8/406; 8/408; 8/435; 8/629; 8/637.1; 8/685; 8/686; 540/145

(58) Field of Classification Search ...................... 8/405, 8/406, 408, 435, 629, 637.1, 685, 686; 540/145
See application file for complete search history.

(56) References Cited

U.S. PATENT DOCUMENTS

| | | | |
|---|---|---|---|
| 2,047,398 A | 7/1936 | Voss et al. | |
| 2,261,002 A | 10/1941 | Ritter | |
| 2,271,378 A | 1/1942 | Searle | |
| 2,273,780 A | 2/1942 | Dittmar | |
| 2,375,853 A | 5/1945 | Kirby et al. | |
| 2,388,614 A | 11/1945 | Kirby et al. | |
| 2,454,547 A | 11/1948 | Bock et al. | |
| 2,528,378 A | 10/1950 | Mannheimer | |
| 2,723,248 A | 11/1955 | Wright | |
| 2,781,354 A | 2/1957 | Mannheimer | |
| 2,798,053 A | 7/1957 | Brown | |
| 2,923,692 A | 2/1960 | Ackerman et al. | |
| 2,961,347 A | 11/1960 | Floyd | |
| 3,206,462 A | 9/1965 | McCarty | |
| 3,227,615 A | 1/1966 | Korden | |
| 3,472,840 A | 10/1969 | Stone et al. | |
| 3,592,581 A * | 7/1971 | Shansky et al. ................ | 8/405 |
| 3,632,559 A | 1/1972 | Matter et al. | |
| 3,770,683 A | 11/1973 | Barabas et al. | |
| 3,836,537 A | 9/1974 | Boerwinkle et al. | |
| 3,874,870 A | 4/1975 | Green et al. | |
| 3,910,862 A | 10/1975 | Barabas et al. | |
| 3,912,808 A | 10/1975 | Sokol | |
| 3,915,921 A | 10/1975 | Schlatzer, Jr. | |
| 3,929,735 A | 12/1975 | Barabas | |
| 3,929,990 A | 12/1975 | Green et al. | |
| 3,966,904 A | 6/1976 | Green et al. | |
| 3,986,825 A | 10/1976 | Sokol | |
| 3,990,459 A | 11/1976 | Papantoniou | |
| 4,001,432 A | 1/1977 | Green et al. | |
| 4,005,193 A | 1/1977 | Green et al. | |
| 4,013,787 A | 3/1977 | Varlerberghe et al. | |
| 4,025,617 A | 5/1977 | Green et al. | |
| 4,025,627 A | 5/1977 | Green et al. | |
| 4,025,653 A | 5/1977 | Green et al. | |
| 4,026,945 A | 5/1977 | Green et al. | |
| 4,027,020 A | 5/1977 | Green et al. | |
| 4,031,307 A | 6/1977 | DeMartino et al. | |
| 4,070,533 A | 1/1978 | Papantoniou et al. | |
| 4,076,912 A | 2/1978 | Papantoniou et al. | |
| 4,128,631 A | 12/1978 | Lundmark et al. | |
| 4,129,711 A | 12/1978 | Viout et al. | |
| 4,131,576 A | 12/1978 | Iovine et al. | |
| 4,137,208 A | 1/1979 | Elliott | |
| 4,166,894 A | 9/1979 | Schaper | |
| 4,223,009 A | 9/1980 | Chakrabarti | |
| 4,237,243 A | 12/1980 | Quack et al. | |
| 4,277,581 A | 7/1981 | Vanlerberghe et al. | |
| 4,282,203 A | 8/1981 | Jacquet et al. | |
| 4,349,532 A | 9/1982 | Vanlerberghe et al. | |
| 4,509,949 A | 4/1985 | Huang et al. | |
| 4,521,504 A | 6/1985 | Sakuma et al. | |
| 4,591,610 A | 5/1986 | Grollier | |
| 4,608,250 A | 8/1986 | Jacquet et al. | |

(Continued)

FOREIGN PATENT DOCUMENTS

DE    2 330 956    1/1974

(Continued)

OTHER PUBLICATIONS

STIC Search Report dated Jun. 19, 2007.*

(Continued)

*Primary Examiner*—Eisa B Elhilo
(74) *Attorney, Agent, or Firm*—Finnegan, Henderson, Farabow, Garrett & Dunner L.L.P.

(57) ABSTRACT

Disclosed herein is the use of at least one compound chosen from porphyrin compounds and phthalocyanin compounds for dyeing human keratin materials. Further, disclosed herein is a composition comprising, in a suitable dyeing medium, at least one compound from porphyrin compounds and phthalocyanin compounds as at least one direct dye, and also to a ready-to-use composition comprising this at least one direct dye. Furthermore, disclosed herein is a dyeing process using the composition or the ready-to-use composition, and also to a device for implementing this process. Finally, disclosed herein are phthalocyanin compounds.

42 Claims, No Drawings

U.S. PATENT DOCUMENTS

| | | | |
|---|---|---|---|
| 4,693,935 A | 9/1987 | Mazurek | |
| 4,728,571 A | 3/1988 | Clemens et al. | |
| 4,761,273 A | 8/1988 | Grollier et al. | |
| 4,823,985 A | 4/1989 | Grollier et al. | |
| 4,839,166 A | 6/1989 | Grollier et al. | |
| 4,957,732 A | 9/1990 | Grollier et al. | |
| 4,972,037 A | 11/1990 | Garbe et al. | |
| 5,009,880 A | 4/1991 | Grollier et al. | |
| 5,139,037 A | 8/1992 | Grollier et al. | |
| 5,158,762 A | 10/1992 | Pierce | |
| 5,196,189 A | 3/1993 | Jacquet et al. | |
| 5,506,315 A | 4/1996 | Meyer et al. | |
| 5,650,137 A | 7/1997 | Nguyen et al. | |
| 5,708,151 A | 1/1998 | Möckli | |
| 5,739,195 A | 4/1998 | Kroker et al. | |
| 5,792,221 A | 8/1998 | Lagrange et al. | |
| 5,958,392 A | 9/1999 | Grollier et al. | |
| 6,087,493 A | 7/2000 | Wheelhouse et al. | |
| 6,120,780 A | 9/2000 | Dupuis et al. | |
| 6,824,570 B2 | 11/2004 | Vidal et al. | |
| 6,881,230 B2 | 4/2005 | Vidal | |
| 6,884,265 B2 | 4/2005 | Vidal et al. | |
| 6,884,267 B2 | 4/2005 | Vidal et al. | |
| 6,893,471 B2 | 5/2005 | Vidal | |
| 7,001,436 B2 | 2/2006 | Vidal et al. | |
| 7,022,143 B2 | 4/2006 | Vidal et al. | |
| 7,060,110 B2 | 6/2006 | Vidal et al. | |
| 7,066,966 B2 | 6/2006 | Cottard et al. | |
| 7,077,873 B2 | 7/2006 | David et al. | |
| 7,261,743 B2 | 8/2007 | Plos et al. | |
| 2003/0084516 A9 | 5/2003 | Kravtchenko et al. | |
| 2004/0141943 A1 | 7/2004 | Mougin et al. | |
| 2004/0200009 A1 | 10/2004 | Vidal | |
| 2004/0237217 A1* | 12/2004 | Desenne et al. | 8/405 |

FOREIGN PATENT DOCUMENTS

| | | |
|---|---|---|
| EP | 0 080 976 | 6/1983 |
| EP | 0 122 324 | 10/1984 |
| EP | 0 173 109 | 3/1986 |
| EP | 0 186 507 | 7/1986 |
| EP | 0 337 354 | 10/1989 |
| EP | 0 395 282 | 10/1990 |
| EP | 0 412 704 | 2/1991 |
| EP | 0 412 707 | 2/1991 |
| EP | 0 503 853 | 9/1992 |
| EP | 0 582 152 | 2/1994 |
| EP | 0 714 954 | 6/1996 |
| EP | 0 815 828 | 1/1998 |
| FR | 1 400 366 | 5/1965 |
| FR | 1 492 597 | 8/1967 |
| FR | 1 564 110 | 4/1969 |
| FR | 1 580 545 | 9/1969 |
| FR | 1 583 363 | 10/1969 |
| FR | 2 077 143 | 10/1971 |
| FR | 2 080 759 | 11/1971 |
| FR | 2 102 113 | 4/1972 |
| FR | 2 162 025 | 7/1973 |
| FR | 2 190 406 | 2/1974 |
| FR | 2 252 840 | 6/1975 |
| FR | 2 265 781 | 10/1975 |
| FR | 2 265 782 | 10/1975 |
| FR | 2 270 846 | 12/1975 |
| FR | 2 280 361 | 2/1976 |
| FR | 2 316 271 | 1/1977 |
| FR | 2 320 330 | 3/1977 |
| FR | 2 336 434 | 7/1977 |
| FR | 2 350 384 | 12/1977 |
| FR | 2 357 241 | 2/1978 |
| FR | 2 368 508 | 5/1978 |
| FR | 2 383 660 | 10/1978 |
| FR | 2 393 573 | 1/1979 |
| FR | 2 413 907 | 8/1979 |
| FR | 2 416 723 | 9/1979 |
| FR | 2 439 798 | 5/1980 |
| FR | 2 470 596 | 6/1981 |
| FR | 2 505 348 | 11/1982 |
| FR | 2 519 863 | 7/1983 |
| FR | 2 542 997 | 9/1984 |
| FR | 2 586 913 | 3/1987 |
| FR | 2 589 476 | 5/1987 |
| FR | 2 598 611 | 11/1987 |
| FR | 1 222 944 | 6/1990 |
| FR | 2 692 572 | 12/1993 |
| FR | 2 807 650 | 10/2001 |
| FR | 2 811 993 | 1/2002 |
| FR | 2 820 032 | 8/2002 |
| FR | 2 822 693 | 10/2002 |
| FR | 2 822 694 | 10/2002 |
| FR | 2 822 696 | 10/2002 |
| FR | 2 822 698 | 10/2002 |
| FR | 2 825 625 | 12/2002 |
| FR | 2 825 702 | 12/2002 |
| FR | 2 829 926 | 3/2003 |
| FR | 2 844 269 | 3/2004 |
| GB | 0 839 805 | 6/1960 |
| GB | 0 922 457 | 4/1963 |
| GB | 1 021 400 | 3/1966 |
| GB | 1 169 862 | 11/1969 |
| GB | 1 334 416 | 10/1973 |
| GB | 1 546 809 | 5/1979 |
| WO | WO 93/23009 | 11/1993 |
| WO | WO 93/23446 | 11/1993 |
| WO | WO 94/12148 | 6/1994 |
| WO | WO 95/00578 | 1/1995 |
| WO | WO 95/01772 | 1/1995 |
| WO | WO 95/15144 | 6/1995 |
| WO | WO 96/06592 | 3/1996 |
| WO | WO 96/10593 | 4/1996 |
| WO | WO 99/13846 * | 3/1999 |
| WO | WO 00/68282 | 11/2000 |
| WO | WO 00/74674 | 12/2000 |
| WO | WO 02/078660 | 10/2002 |
| WO | WO 02/100369 | 12/2002 |
| WO | WO 02/100834 | 12/2002 |

OTHER PUBLICATIONS

French Search Report for FR 04/53219, (French priority application to the present application), dated Aug. 12, 2005.
English language Derwent Abstract of EP 0 080 976, Jun. 8, 1983.
English language Derwent Abstract of FR 2 357 241, Feb. 3, 1978.
English language Derwent Abstract of FR 2 589 476, May 7, 1987.
Davidson, R. "Handbook of Water-Soluble Gums and Resins", McGraw Hill (1980).
Fonnum, G. et al. "Associative Thickeners. Part I: Synthesis, Rheology, and Aggregation Behavior", Colloid Polym. Sci. 271: 380-389, (1993).
Kadish, K. et al. "Applications of Phthalocyanines", The Porphyrin Handbook, vol. 19, pp. 105-149, Academic Press: (2003).
Santra, S. et al. "Cis-Pyridyl Core- Modified Porphyrins for the Synthesis of Cationic Water-Soluble Porphyrins and Unsymmetrical Non-Covalent Porphyrin Arrays", Tetrahedron, vol. 59, pp. 2353-2362, (2003).

* cited by examiner

USE OF AT LEAST ONE COMPOUND CHOSEN FROM PORPHYRIN COMPOUNDS AND PHTHALOCYANIN COMPOUNDS FOR DYEING HUMAN KERATIN MATERIALS, COMPOSITIONS COMPRISING THEM, A DYEING PROCESS, AND COMPOUNDS THEREFOR

CROSS-REFERENCE TO RELATED APPLICATIONS

This application claims benefit of U.S. Provisional Application No. 60/681,459, filed May 17, 2005, the contents of which are incorporated herein by reference. This application also claims benefit of priority under 35 U.S.C. § 119 to French Patent Application No. 0453219, filed Dec. 23, 2004, the contents of which are also incorporated herein by reference.

FIELD OF THE INVENTION

Disclosed herein is the use of at least one compound chosen from porphyrin compounds and phthalocyanin compounds for dyeing human keratin materials. Also disclosed herein is a composition comprising, in a suitable dyeing medium, at least one compound chosen from porphyrin compounds and phthalocyanin compounds as an at least one direct dye, and also a ready-to-use composition comprising this at least one direct dye. Further disclosed herein is a dyeing process using the composition or the ready-to-use composition, and also a device for implementing this process. Finally, disclosed herein are phthalocyanin compounds per se.

SUMMARY OF THE INVENTION

Certain embodiments disclosed herein relate to the field of dyeing human keratin fibers, such as the hair.

Moreover, certain embodiments disclosed herein relate to the field of "semi-permanent" dyeing, also known as direct dyeing, which comprises applying a dye composition comprising, as dye, at least one colored molecule that penetrates by diffusion into the fiber and/or remains adsorbed on its surface. The composition may optionally be applied in the presence of at least one oxidizing agent. In the latter case, this may be referred to as direct dyeing under lightening conditions.

Problems may be encountered with blue, green, or even brown direct dyes. For example, such direct dyes may show insufficient stability towards light or towards chemical agents, for instance oxidizing agents and/or reducing agents.

One embodiment disclosed herein is the use of compounds other than those used hitherto, as direct dyes for dyeing human keratin materials, such as fibers, which allow access to blue, green, and/or brown shades that are stable and fast, and that moreover do not change in color over time.

Thus, one embodiment disclosed herein is the use of at least one non-metallic or metallic cationic compound chosen from porphyrin compounds and phthalocyanin compounds comprising as the metal element at least one metal or metal ion chosen from columns IA and IIA of the Periodic Table of the Elements, zinc, and silicon, as a direct dye for dyeing human keratin materials, such as fibers.

Another embodiment disclosed herein is a dye composition comprising, in a medium that is suitable for dyeing human keratin materials, at least one non-metallic or metallic cationic compound chosen from porphyrin compounds and phthalocyanin compounds comprising as the metal element at least one metal or metal ion chosen from columns IA and IIA of the Periodic Table of the Elements, zinc, and silicon, as a direct dye, and at least one surfactant and/or at least one polymer.

Another embodiment disclosed herein comprises a ready-to-use composition comprising at least one non-metallic or metallic cationic compound chosen from porphyrin compounds and phthalocyanin compounds comprising as the metal element at least one metal or metal ion chosen from columns IA and IIA of the Periodic Table of the Elements, zinc, and silicon, as a direct dye, and at least one oxidizing agent.

A further embodiment disclosed herein is a process for dyeing human keratin materials, such as fibers, comprising applying the composition disclosed herein in the absence of an oxidizing agent, and optionally with final rinsing.

According to another embodiment disclosed herein, the process comprises applying a composition disclosed herein, in the presence of at least one oxidizing agent, and leaving the composition to act for a time sufficient to obtain the desired coloration.

Furthermore, disclosed herein is a multi-compartment device for dyeing keratin materials, such as fibers, comprising at least one first compartment with, in a medium that is suitable for dyeing human keratin fibers, the at least one non-metallic or metallic cationic compound chosen from porphyrin compounds and phthalocyanin compounds comprising as the metal element at least one metal or metal ion chosen from columns IA and IIA of the Periodic Table of the Elements, zinc, and silicon, optionally at least one additional direct dye, optionally at least one oxidation base, and/or at least one coupler, wherein these compounds are present in at least one composition, which may or may not be combined, and, moreover, a second compartment with a composition comprising, in a medium that is suitable for dyeing human keratin fibers, at least one oxidizing agent.

It has been noted that at least one non-metallic or metallic cationic compound chosen from porphyrin compounds and phthalocyanin compounds may make it possible to obtain good, non-selective coloration of the treated material, this coloration being color-fast with respect to washing, for example, irrespective of the pH at which the dyeing process is performed.

It has also been found that this type of compound may give good results under lightening or non-lightening conditions.

The at least one non-metallic or metallic cationic compound chosen from porphyrin compounds and phthalocyanin compounds as defined previously may constitute an advantageous alternative to the direct dyes conventionally used, such as for dyeing sensitized hair.

The reason for this may be that, on this type of hair, the dyes disclosed herein may show very good resistance to repeated shampooing.

In general, the porphyrins and phthalocyanins used in the context of embodiments disclosed herein may simultaneously present many advantages, such as allowing strong and uniform dyeing of the hair to be obtained, even under lightening conditions (presence of at least one oxidizing agent and at least one alkaline agent). Furthermore, their chemical structure, for example their high molar mass, and also the presence of at least one cationic charge, may limit their transcutaneous penetration.

However, other advantages and characteristics of embodiments disclosed herein will emerge more clearly on reading the description and the examples that follow.

It is pointed out that, unless otherwise indicated, the limits of the ranges of values that will be given are included in these ranges.

Furthermore, the Periodic Table of the Elements to which reference is made corresponds to the Table published in the 12th edition of the "Merck Index".

Moreover, unless more specifically indicated, the terms substituted alkyl, alkenyl, or alkynyl radical denote an alkyl, alkenyl, or alkynyl radical bearing at least one of the following entities:

hydroxyl groups;

linear or branched $C_1$-$C_{10}$ alkoxy radicals;

amino radicals;

amino radicals substituted with at least one linear or branched $C_1$-$C_{10}$ alkyl radical optionally bearing at least one group chosen from hydroxyl groups and linear or branched $C_1$-$C_{10}$ alkoxy groups, the said radicals optionally forming, together with the nitrogen atom to which they are attached, a 5- or 6-membered heterocycle optionally comprising another hetero atom, such as nitrogen and oxygen atoms;

amino radicals subsituted with at least one radical chosen from linear or branched $C_6$ aryl radicals and ($C_6$)aryl ($C_1$-$C_{10}$)alkyl radicals; and ammonium radicals bearing three identical or different radicals chosen from hydrogen atoms and linear or branched $C_1$-$C_{10}$ alkyl radicals optionally bearing at least one group chosen from hydroxyl groups and linear or branched $C_1$-$C_{10}$ alkoxy groups, wherein two of the alkyl radicals may optionally form, together with the nitrogen atom to which they are attached, a 5- or 6-membered heterocycle optionally comprising another hetero atom, such as a heteroatom chosen from nitrogen, oxygen, and sulfur atoms.

In addition, unless more specifically indicated, the term substituted aryl radical denotes an aryl radical bearing at least one of the following groups:

hydroxyl groups;

linear or branched $C_1$-$C_{10}$ alkoxy radicals;

amino radicals;

amino radicals substituted with at least one linear or branched $C_1$-$C_{10}$ alkyl radical optionally bearing at least one group chosen from hydroxyl groups and linear or branched $C_1$-$C_{10}$ alkoxy groups, the said radicals optionally forming, together with the nitrogen atom to which they are attached, a 5- or 6-membered heterocycle optionally comprising another hetero atom, such as a heteroatom chosen from nitrogen, oxygen, and sulfur atoms;

amino radicals substituted with at least one radical chosen from linear or branched $C_6$ aryl radicals and ($C_6$)aryl ($C_1$-$C_{10}$)alkyl radicals;

ammonium radicals bearing three identical or different radicals chosen from hydrogen atoms, linear or branched $C_1$-$C_{10}$ alkyl radicals optionally bearing at least one group chosen from hydroxyl groups and linear or branched $C_1$-$C_{10}$ alkoxy groups, two of the alkyl radicals optionally forming, together with the nitrogen atom to which they are attached, a 5- or 6-membered heterocycle optionally comprising another hetero atom, such as a heteroatom chosen from nitrogen, oxygen, and sulfur atoms;

radicals chosen from —$CONH_2$ and —NHCOR in which R represents a linear or branched $C_1$-$C_{10}$ alkyl radical;

saturated or unsaturated, 5- or 6-membered, optionally substituted heterocycles comprising at least one hetero atom chosen from nitrogen, oxygen, and sulfur;

nitro radicals; and halogen atoms, such as chlorine.

It is pointed out that the indications given above are valid whether it is a matter of a simple or compound radical (for example alkoxy, arylalkyl, alkylaryl, etc.).

Furthermore, as used herein the term "substituted heterocyclic radical" denotes a heterocyclic radical bearing at least one group chosen from the following groups:

hydroxyl groups;

linear or branched $C_1$-$C_{10}$ alkoxy radicals;

amino radicals;

amino radicals substituted with at least one linear or branched $C_1$-$C_{10}$ alkyl radical optionally bearing at least one group chosen from hydroxyl groups and linear or branched $C_1$-$C_{10}$ alkoxy groups, the said radicals optionally forming, together with the nitrogen atom to which they are attached, a 5- or 6-membered heterocycle optionally comprising another hetero atom, such as a heteroatom chosen from nitrogen, oxygen, and sulfur atoms;

amino radicals substituted with at least one radical chosen from linear or branched $C_6$ aryl radicals and ($C_6$)aryl ($C_1$-$C_{10}$)alkyl radicals;

ammonium radicals bearing three identical or different radicals chosen from hydrogen atoms and linear or branched $C_1$-$C_{10}$ alkyl radicals optionally bearing at least one group chosen from hydroxyl groups and linear or branched $C_1$-$C_{10}$ alkoxy groups, wherein two of the alkyl radicals optionally form, together with the nitrogen atom to which they are attached, a 5- or 6-membered heterocycle optionally comprising another hetero atom, such as heteroatoms chosen from nitrogen, oxygen, and sulfur atoms; and halogen atoms, such as chlorine.

As indicated previously, one embodiment disclosed herein is the use of non-metallic or metallic cationic compounds chosen from porphyrin compounds and phthalocyanin compounds comprising as the metal element at least one metal or metal ion chosen from columns IA and IIA, zinc, and silicon, as a direct dye for human keratin materials, such as for human keratin fibers, for instance the hair.

In certain embodiments, the metallic or non-metallic cationic compound chosen from porphyrin compounds and phthalocyanin compounds does not contain any metal liable to degrade oxidizing agents. It should be noted that the said compound may not comprise such metals in the counterions that are associated therewith.

Among the metals liable to degrade oxidizing agents, such as hydrogen peroxide, mention may be made of transition metals (i.e. those for which the electron shell is incomplete). Additional examples that may be mentioned include copper, iron, cobalt, and nickel.

DETAILED DESCRIPTION OF THE INVENTION

According to one embodiment, the metallic or non-metallic cationic compound chosen from porphyrin compounds and phthalocyanin compounds is soluble in the composition, at the content used, at room temperature and atmospheric pressure.

Among the metallic or non-metallic cationic porphyrin compounds that may be used in accordance with embodiments disclosed herein, mention may be made of compounds corresponding to formula (1) below, and the tautomeric forms thereof, bearing at least one cationic charge:

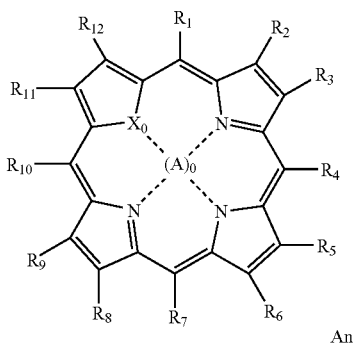

in which:

the radicals $R_1$ to $R_{12}$, which may be identical or different, are groups chosen from at least one of the following:

hydrogen atoms;

linear or branched $C_1$-$C_{30}$ alkyl radicals; linear or branched $C_2$-$C_{30}$ alkenyl radicals; linear or branched $C_2$-$C_{30}$ alkynyl radicals;

wherein the said alkyl, alkenyl, and alkynyl radicals are optionally substituted with at least one monovalent group chosen from the following groups:

hydroxyl groups;

amino groups;

amino groups substituted with one or two linear or branched $C_1$-$C_{10}$ alkyl radicals, which may be identical or different, optionally bearing at least one group chosen from hydroxyl groups and linear or branched $C_1$-$C_{10}$ alkoxy groups;

ammonium groups substituted with one, two, or three linear or branched $C_1$-$C_{10}$ alkyl radicals, which may be identical or different, optionally bearing at least one group chosen from hydroxyl groups and linear or branched $C_1$-$C_{10}$ alkoxy groups;

hydrogenocarbonyl (—COH) groups; and optionally substituted 5- or 6-membered heterocycles, comprising at least one hetero atom, for instance a heteroatom chosen from oxygen and nitrogen, optionally bearing at least one cationic charge, wherein the said heterocycle is optionally fused with an aromatic nucleus, which may be 6-membered;

wherein at least one of the said alkyl, alkenyl, and alkynyl radicals is optionally interrupted with at least one divalent group chosen from the following groups:

oxygen atoms;

amino groups;

amino groups substituted with a linear or branched $C_1$-$C_{10}$ alkyl radical, optionally bearing at least one group chosen from hydroxyl groups and linear or branched $C_1$-$C_{10}$ alkoxy groups;

ammonium groups substituted with one or two linear or branched $C_1$-$C_{10}$ alkyl radicals, which may be identical or different, optionally bearing at least one group chosen from hydroxyl groups and linear or branched $C_1$-$C_{10}$ alkoxy groups;

carbonyl (—CO—) groups; and optionally substituted 5- or 6-membered heterocycles, comprising at least one hetero atom, for instance a heteroatom chosen from oxygen and nitrogen, optionally bearing at least one cationic charge;

optionally substituted $C_6$-$C_{30}$ aryl radicals; optionally substituted $(C_1$-$C_{30})$alkyl$(C_6$-$C_{30})$aryl radicals; optionally substituted $(C_6$-$C_{30})$aryl$(C_1$-$C_{30})$alkyl radicals;

hydroxyl groups;

optionally substituted linear or branched $C_1$-$C_{30}$ alkoxy radicals;

amino radicals; amino radicals bearing at least one optionally substituted linear or branched $C_1$-$C_{30}$ alkyl radical;

radicals chosen from —$SO_2$—$NH_2$, —$SO_2$NH-alkyl, and —NH—$SO_2$-alkyl radicals, in which the alkyl radical is an optionally substituted linear or branched $C_1$-$C_{30}$ alkyl; and optionally cationic, optionally aromatic, 5- or 6-membered heterocyclic radicals, comprising at least one nitrogen atom, and optionally at least one other hetero atom, which may be identical or different, wherein the heterocyclic radical is optionally substituted;

wherein at least one of the radicals $R_1$ to $R_{12}$ bears at least one cationic charge;

$X_0$ is chosen from nitrogen, oxygen, and sulfur;

A is chosen from at least one metal or metal ion chosen from columns IA and IIA of the Periodic Table of the Elements, such as sodium, potassium, magnesium, and calcium; zinc; and silicon;

p is chosen from 0, 1, and 2, depending on the nature of the element A; and

An is at least one cosmetically acceptable anion that compensates the total cationic charge of the compound.

In certain embodiments, the radicals $R_2$, $R_3$, $R_5$, $R_6$, $R_8$, $R_9$, $R_{11}$, and $R_{12}$, which may be identical or different, are chosen from:

hydrogen atoms;

linear or branched $C_1$-$C_{12}$ alkyl radicals, such as $C_1$-$C_8$ alkyl radicals, optionally substituted with at least one ammonium group substituted with one, two, or three linear or branched $C_1$-$C_8$ alkyl radicals, which may be identical or different, optionally bearing at least one group chosen from hydroxyl groups and linear or branched $C_1$-$C_8$ alkoxy groups;

—$SO_2$NH-alkyl radicals in which the alkyl radical is a linear or branched $C_1$-$C_{12}$ alkyl, optionally substituted with at least one ammonium group substituted with one, two, or three linear or branched $C_1$-$C_8$ alkyl radicals, which may be identical or different, optionally bearing at least one group chosen from hydroxyl groups and linear or branched $C_1$-$C_8$ alkoxy groups;

optionally substituted phenyl radicals;

linear or branched $C_1$-$C_{12}$ alkoxy radicals, such as $C_1$-$C_8$ alkoxy radicals;

amino radicals substituted with one or two linear or branched $C_1$-$C_{10}$ alkyl radicals, which may be identical or different, optionally bearing at least one group chosen from hydroxyl groups and linear or branched $C_1$-$C_8$ alkoxy groups; and optionally substituted 5- or 6-membered heterocycles, comprising at least one hetero atom, such as oxygen and nitrogen, optionally bearing at least one cationic charge.

Furthermore, in accordance with one embodiment disclosed herein, the radicals $R_1$, $R_4$, $R_7$, and $R_{10}$, which may be identical or different, are chosen from at least one of the following radicals:

pyridinium radicals optionally attached via one of the carbon atoms of the heterocycle;

optionally substituted quinolinium radicals; and phenyl radicals optionally substituted with at least one of the following:

ammonium groups substituted with one, two, or three linear or branched $C_1$-$C_8$ alkyl radicals, which may be identical or different, optionally bearing at least one group chosen from hydroxyl groups and linear or branched $C_1$-$C_8$ alkoxy groups;
chlorine atoms,
nitro groups,
hydroxyl groups,
linear or branched $C_1$-$C_8$ alkoxy radicals;
—$CONH_2$ groups,
groups —CO—NHR with R representing a linear or branched $C_1$-$C_8$ alkyl radical; and
optionally substituted 5- or 6-membered heterocycles, comprising at least one hetero atom, such as oxygen and nitrogen, optionally bearing at least one cationic charge.

According to one embodiment disclosed herein, when A represents a metal that is not monovalent, such as in the case of silicon, this metal may be covalently bonded to a hydrocarbon-based radical optionally bearing at least one cationic charge. In this case, the said hydrocarbon-based radical is chosen from linear or branched $C_1$-$C_{30}$ alkyl radicals; linear or branched $C_2$-$C_{30}$ alkenyl radicals; and linear or branched $C_2$-$C_{30}$ alkynyl radicals, wherein the said alkyl, alkenyl, and alkynyl radicals are optionally substituted and/or interrupted with at least one oxygen atom; carbonyl groups; groups —NR— and —$N^+R_2$ in which the radicals R, which may be identical or different, represent hydrogen; optionally substituted linear or branched $C_1$-$C_{30}$ alkyl radicals; optionally substituted 5- or 6-membered heterocycles comprising at least one hetero atom, such as oxygen and nitrogen, optionally bearing at least one cationic charge.

Among the non-metallic or metallic cationic phthalocyanin compounds that may be used in the embodiments disclosed herein, mention may be made of the compounds corresponding to formula (2) below, and the tautomeric forms thereof, bearing at least one cationic charge:

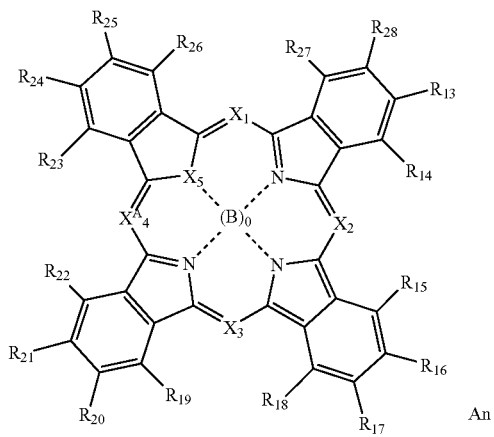

in which:
the radicals $R_{13}$ to $R_{28}$, which may be identical or different, are chosen from at least one of the following:
hydrogen atoms;
linear or branched $C_1$-$C_{30}$ alkyl radicals; linear or branched $C_2$-$C_{30}$ alkenyl radicals; and linear or branched $C_2$-$C_{30}$ alkynyl radicals, wherein the said alkyl, alkenyl, and alkynyl radicals are optionally substituted with at least one monovalent group chosen from at least one of the following groups:
hydroxyl groups;
amino groups;
amino groups substituted with one or two linear or branched $C_1$-$C_{10}$ alkyl radicals, which may be identical or different, optionally bearing at least one group chosen from hydroxyl groups and linear or branched $C_1$-$C_{10}$ alkoxy groups;
ammonium groups substituted with one, two, or three linear or branched $C_1$-$C_{10}$ alkyl radicals, which may be identical or different, optionally bearing at least one group chosen from hydroxyl groups and linear or branched $C_1$-$C_{10}$ alkoxy groups;
hydrogenocarbonyl (—COH) groups; and
optionally substituted 5- or 6-membered heterocycles, comprising at least one hetero atom, such as oxygen and nitrogen, optionally bearing at least one cationic charge, the said heterocycle optionally being fused with an aromatic nucleus, which is optionally 6-membered;
and/or wherein the said alkyl, alkenyl, and alkynyl radicals are optionally interrupted with at least one divalent group chosen from the following groups:
oxygen atoms;
amino groups;
amino groups substituted with at least one linear or branched $C_1$-$C_{10}$ alkyl radicals, optionally bearing at least one group chosen from hydroxyl groups and linear or branched $C_1$-$C_{10}$ alkoxy groups;
ammonium groups substituted with one or two linear or branched $C_1$-$C_{10}$ alkyl radicals, which may be identical or different, optionally bearing at least one group chosen from hydroxyl groups and linear or branched $C_1$-$C_{10}$ alkoxy groups;
carbonyl (—CO—) groups; and
optionally substituted 5- or 6-membered heterocycles, comprising at least one hetero atom, such as oxygen and nitrogen, optionally bearing at least one cationic charge;
optionally substituted $C_6$-$C_{30}$ aryl radicals; optionally substituted ($C_1$-$C_{30}$)alkyl($C_6$-$C_{30}$)aryl radicals; optionally substituted ($C_6$-$C_{30}$)aryl($C_1$-$C_{30}$)alkyl radicals;
hydroxyl groups;
optionally substituted linear or branched $C_1$-$C_{30}$ alkoxy radicals;
amino radicals; amino radicals bearing at least one optionally substituted linear or branched $C_1$-$C_{30}$ alkyl radical;
radicals —$SO_2$—$NH_2$, —$SO_2$NH-alkyl, and —NH—$SO_2$-alkyl, in which the alkyl radical is an optionally substituted linear or branched $C_1$-$C_{30}$ alkyl; and
optionally cationic, optionally aromatic, 5- or 6-membered heterocyclic radicals, comprising at least one nitrogen atom, and optionally at least one other hetero atom, which may be identical or different; the said heterocyclic radical being optionally substituted;
wherein at least one of the radicals $R_{13}$ to $R_{28}$ bears at least one cationic charge;
$X_1$ to $X_4$, which may be identical or different, are chosen from nitrogen atoms and groups —$CR_{29}$, with $R_{29}$ having the same definition as the abovementioned $R_{13}$ to $R_{28}$;
$X_5$ is chosen from nitrogen, oxygen, and sulfur;
B is chosen from metals or metal ions chosen from column IA and IIA of the Periodic Table of the Elements, such as sodium, potassium, magnesium, and calcium, zinc, and silicon;
q is chosen from 0, 1, and 2 depending on the nature of the element B;

An is chosen from at least one cosmetically acceptable anion that compensate the total cationic charge of the compound.

In certain embodiments, the radicals $R_{13}$ to $R_{28}$, which may be identical or different, are chosen from at least one of the following:

hydrogen atoms;

linear or branched $C_1$-$C_{12}$ alkyl radicals, such as $C_1$-$C_8$ alkyl radicals, optionally substituted with at least one ammonium group substituted with one, two, or three linear or branched $C_1$-$C_8$ alkyl radicals, which may be identical or different, optionally bearing at least one group chosen from hydroxyl groups and linear or branched $C_1$-$C_8$ alkoxy groups;

—$SO_2NH$-alkyl radicals in which the alkyl radical is a linear or branched $C_1$-$C_{12}$ alkyl, optionally substituted with at least one ammonium group substituted with one, two, or three linear or branched $C_1$-$C_8$ alkyl radicals, which may be identical or different, optionally bearing at least one group chosen from hydroxyl groups and linear or branched $C_1$-$C_8$ alkoxy groups;

linear or branched $C_1$-$C_{12}$ alkoxy radicals, such as $C_1$-$C_8$ alkoxy radicals;

amino radicals substituted with one or two linear or branched $C_1$-$C_{10}$ alkyl radicals, which may be identical or different, optionally bearing at least one group chosen from hydroxyl groups and linear or branched $C_1$-$C_8$ alkoxy groups;

optionally substituted 5- or 6-membered heterocycles, comprising at least one hetero atom such as oxygen and nitrogen, optionally bearing at least one cationic charge, such as pyridinium and quinolinium radicals; and phenyl radicals optionally substituted with at least one of the following:
  ammonium groups substituted with one, two, or three linear or branched $C_1$-$C_8$ alkyl radicals, which may be identical or different, optionally bearing at least one group chosen from hydroxyl groups and linear or branched $C_1$-$C_8$ alkoxy groups;
  chlorine atoms,
  nitro groups,
  hydroxyl groups,
  linear or branched $C_1$-$C_8$ alkoxy radicals;
  —$CONH_2$ groups,
  groups —CO—NHR with R representing a linear or branched $C_1$-$C_8$ alkyl radical; and
  optionally substituted 5- or 6-membered heterocycles, comprising at least one hetero atom such as oxygen and nitrogen, optionally bearing at least one cationic charge.

As regards the radicals $R_{29}$, these radicals, which may be identical or different, may be chosen from at least one of the following:

pyridinium radicals optionally attached via one of the carbon atoms of the heterocycle;

optionally substituted quinolinium radicals;

phenyl radicals optionally substituted with at least one of the following:
  ammonium groups substituted with one, two, or three linear or branched $C_1$-$C_8$ alkyl radicals, which may be identical or different, optionally bearing at least one group chosen from hydroxyl groups and linear or branched $C_1$-$C_8$ alkoxy groups;
  chlorine atoms,
  nitro groups,
  hydroxyl groups,
  linear or branched $C_1$-$C_8$ alkoxy radicals,
  —$CONH_2$ groups,
  groups —CO—NHR with R representing a linear or branched $C_1$-$C_8$ alkyl radical, and
  optionally substituted 5- or 6-membered heterocycles, comprising at least one hetero atom such as oxygen and nitrogen, optionally bearing at least one cationic charge.

As regards the synthesis of the compounds of formulae (1) and (2), reference may be made to U.S. Pat. No. 6,087,493, patent application WO 00/74674, and also to "The Porphyrin Handbook", Karl M. Kadish, Kevin M. Smith, Roger Guilard: vol. 19, p. 105, edition 2003, and the publication "Cis-Pyridyl Core-Modified Porphyrins for the Synthesis of Cationic Water-Soluble Porphyrins and Unsymmetrical Non-Covalent Porphyrin Arrays", Sangita Santra, Duraisamy Kumaresan, Neeraj Agarwal, D. Mangalampalli Ravikanth, Tetrahedron (2003) 2353-2362.

Moreover, in the above two formulae, a cosmetically acceptable anion may be chosen from chlorides, bromides, iodides, phosphates, sulfates, methyl sulfate, ethyl sulfate, tosylates, benzenesulfonates, citrates, succinates, tartrates, lactates, and acetates.

In certain embodiments, the content of at least one non-metallic cationic compound as described above, in a dye composition, represents from 0.005% to 20% by weight, such as from 0.05% to 10% by weight or from 0.1% to 8% by weight, relative to the total weight of the composition.

The medium for these dye compositions that is suitable for dyeing keratin materials may comprise water or a mixture of water and of at least one common organic solvent.

In certain embodiments, the at least one organic solvent, when it is present, is chosen from linear or branched, for example saturated, monoalcohols and polyols, containing from 2 to 10 carbon atoms, such as ethyl alcohol, isopropyl alcohol, hexylene glycol (2-methyl-2,4-pentanediol), neopentyl glycol, and 3-methyl-1,5-pentanediol; aromatic alcohols such as benzyl alcohol and phenylethyl alcohol; glycols and glycol ethers, for instance ethylene glycol monomethyl ether, ethylene glycol monoethyl ether, and ethylene glycol monobutyl ether, propylene glycol and ethers thereof, for instance propylene glycol monomethyl ether, butylene glycol, and dipropylene glycol; and also diethylene glycol alkyl ethers, such as $C_1$-$C_4$ alkyl ethers, for instance diethylene glycol monoethyl ether and monobutyl ether.

The solvents described above, when they are present, may be present in an amount ranging from 1% to 40% by weight, such as from 5% to 30% by weight, relative to the total weight of the dye composition.

The dye composition may also comprise at least one additional direct dye other than the at least one non-metallic cationic compound chosen from porphyrin compounds and phthalocyanin compounds.

For example, the at least one additional direct dye may be nonionic, cationic, or anionic.

Non-limiting examples that may be mentioned include nitrobenzene dyes, azo, azomethine, methine, tetraazapentamethine, anthraquinone, naphthoquinone, benzoquinone, phenothiazine, indigoid, xanthene, phenanthridine, phthalocyanin, and triarylmethane-based dyes and natural dyes.

It may be chosen, for example, from at least one of the following red and orange nitrobenzene dyes:
1-hydroxy-3-nitro-4-N-(γ-hydroxypropyl)aminobenzene,
N-(β-hydroxyethyl)amino-3-nitro-4-aminobenzene,
1-amino-3-methyl-4-N-(β-hydroxyethyl)amino-6-nitrobenzene,
1-hydroxy-3-nitro-4-N-(β-hydroxyethyl)aminobenzene,
1,4-diamino-2-nitrobenzene,
1-amino-2-nitro-4-methylaminobenzene, N-(β-hydroxyethyl)-2-nitro-para-phenylenediamine,
1-amino-2-nitro-4-(β-hydroxyethyl)amino-5-chlorobenzene,
2-nitro-4-aminodiphenylamine,
1-amino-3-nitro-6-hydroxybenzene,
1-(β-aminoethyl)amino-2-nitro-4-(β-hydroxyethyloxy)benzene,
1-(β,γ-dihydroxypropyl)oxy-3-nitro-4-(β-hydroxyethyl)aminobenzene,
1-hydroxy-3-nitro-4-aminobenzene,
1-hydroxy-2-amino-4,6-dinitrobenzene,
1-methoxy-3-nitro-4-(β-hydroxyethyl)aminobenzene,
2-nitro-4'-hydroxydiphenylamine, and
1-amino-2-nitro-4-hydroxy-5-methylbenzene.

The at least one additional direct dye may also be chosen from yellow and green-yellow nitrobenzene direct dyes; mention may be made, for example, of the compounds chosen from:
1-β-hydroxyethyloxy-3-methylamino-4-nitrobenzene,
1-methylamino-2-nitro-5-(β,γ-dihydroxypropyl)oxybenzene,
1-(β-hydroxyethyl)amino-2-methoxy-4-nitrobenzene,
1-(β-aminoethyl)amino-2-nitro-5-methoxybenzene,
1,3-di(β-hydroxyethyl)amino-4-nitro-6-chlorobenzene,
1-amino-2-nitro-6-methylbenzene,
1-(β-hydroxyethyl)amino-2-hydroxy-4-nitrobenzene,
N-(β-hydroxyethyl)-2-nitro-4-trifluoromethylaniline,
4-(β-hydroxyethyl)amino-3-nitrobenzenesulfonic acid,
4-ethylamino-3-nitrobenzoic acid,
4-(β-hydroxyethyl)amino-3-nitrochlorobenzene,
4-(β-hydroxyethyl)amino-3-nitromethylbenzene,
4-(β,γ-dihydroxypropyl)amino-3-nitrotrifluoromethylbenzene,
1-(β-ureidoethyl)amino-4-nitrobenzene,
1,3-diamino-4-nitrobenzene,
1-hydroxy-2-amino-5-nitrobenzene,
1-amino-2-[tris(hydroxymethyl)methyl]amino-5-nitrobenzene,
1-(β-hydroxyethyl)amino-2-nitrobenzene, and
4-(β-hydroxyethyl)amino-3-nitrobenzamide.

Mention may also be made of blue and violet nitrobenzene direct dyes, for instance:
1-(β-hydroxyethyl)amino-4-N,N-bis(β-hydroxyethyl)amino-2-nitrobenzene,
1-(γ-hydroxypropyl)amino-4,N,N-bis(β-hydroxyethyl)amino-2-nitrobenzene,
1-(β-hydroxyethyl)amino-4-(N-methyl-N-β-hydroxyethyl)amino-2-nitrobenzene,
1-(β-hydroxyethyl)amino-4-(N-ethyl-N-β-hydroxyethyl)amino-2-nitrobenzene,
1-(β,γ-dihydroxypropyl)amino-4-(N-ethyl-N-β-hydroxyethyl)amino-2-nitrobenzene,
2-nitro-para-phenylenediamines having the following formula:

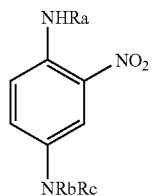

in which:
Rb is chosen from $C_1$-$C_4$ alkyl radicals, β-hydroxyethyl radicals, β-hydroxypropyl radicals, and γ-hydroxypropyl radicals;
Ra and Rc, which may be identical or different, are chosen from β-hydroxyethyl radicals, β-hydroxypropyl radicals, γ-hydroxypropyl radicals, and β,γ-dihydroxypropyl radicals, at least one of the radicals Rb, Rc, or Ra representing α-hydroxypropyl radical and Rb and Rc not simultaneously being a β-hydroxyethyl radical when Rb is a γ-hydroxypropyl radical, such as those described in French Patent No. FR 2 692 572.

Among the azo direct dyes that may be used according to embodiments disclosed herein, mention may be made of the cationic azo dyes described, for example, in patent documents WO 95/15144, WO 95/01772, EP 714 954, FR 2 822 696, FR 2 825 702, FR 2 825 625, FR 2 822 698, FR 2 822 693, FR 2 822 694, FR 2 829 926, FR 2 807 650, WO 02/078 660, WO 02/100 834, WO 02/100 369, and FR 2 844 269.

Among these compounds, mention may be made of the following dyes:
1,3-dimethyl-2-[[4-(dimethylamino)phenyl]azo]-1H-imidazolium chloride,
1,3-dimethyl-2-[(4-aminophenyl)azo]-1H-imidazolium chloride, and
1-methyl-4-[(methylphenylhydrazono)methyl]pyridinium methyl sulfate.

Among the azo direct dyes that may also be mentioned are the following dyes described in the Colour Index International 3rd edition:
Disperse Red 17
Acid Yellow 9
Acid Black 1
Basic Red 22
Basic Red 76
Basic Yellow 57
Basic Brown 16
Acid Yellow 36
Acid Orange 7
Acid Red 33
Acid Red 35
Basic Brown 17
Acid Yellow 23
Acid Orange 24, and
Disperse Black 9.

Mention may also be made of 1-(4'-aminodiphenylazo)-2-methyl-4-[bis(β-hydroxyethyl)amino]benzene, and 4-hydroxy-3-(2-methoxyphenylazo)-1-naphthalenesulfonic acid.

Among the quinone direct dyes that may be mentioned are the following dyes:
Disperse Red 15
Solvent Violet 13
Acid Violet 43
Disperse Violet 1
Disperse Violet 4
Disperse Blue 1
Disperse Violet 8
Disperse Blue 3
Disperse Red 11
Acid Blue 62
Disperse Blue 7
Basic Blue 22
Disperse Violet 15, and
Basic Blue 99
and also the following compounds:
1-N-methylmorpholiniumpropylamino-4-hydroxyanthraquinone 1-aminopropylamino-4-methylaminoanthraquinone
1-aminopropylaminoanthraquinone
5-β-hydroxyethyl-1,4-diaminoanthraquinone
2-aminoethylaminoanthraquinone, and
1,4-bis(β,γ-dihydroxypropylamino)anthraquinone.

Among the azine dyes that may be mentioned are the following compounds:
Basic Blue 17, and
Basic Red 2.

Among the cationic methine direct dyes, mention may also be made of Basic Red 14, Basic Yellow 13, and Basic Yellow 29.

Among the triarylmethane dyes that may be used according to certain embodiments disclosed herein, mention may be made of the following compounds:
Basic Green 1
Acid Blue 9
Basic Violet 3
Basic Violet 14
Basic Blue 7
Acid Violet 49
Basic Blue 26, and
Acid Blue 7.

Among the indoamine dyes that may be used according to certain embodiments disclosed herein, mention may be made of the following compounds:
2-β-hydroxyethylamino-5-[bis(β-4'-hydroxyethyl)amino] anilino-1,4-benzoquinone;
2-β-hydroxyethylamino-5-(2'-methoxy-4'-amino)anilino-1,4-benzoquinone;
3-N(2'-chloro-4'-hydroxy)phenylacetylamino-6-methoxy-1,4-benzoquinoneimine;
3-N(3'-chloro-4'-methylamino)phenylureido-6-methyl-1,4-benzoquinoneimine; and
3-[4'-N-(ethylcarbamylmethyl)amino]phenylureido-6-methyl-1,4-benzoquinoneimine.

The composition may also comprise at least one natural direct dye, for instance lawsone, juglone, alizarin, purpurin, carminic acid, kermesic acid, purpurogallin, protocatechaldehyde, indigo, isatin, curcumin, spinulosin, and apigenidin. Extracts or decoctions containing these natural dyes, for example henna-based poultices and extracts, may also be used.

The at least one additional direct dye may be present in an amount ranging from 0.0005% to 12% by weight relative to the total weight of the composition, such as from 0.005% to 6% by weight relative to the total weight of the composition.

The composition disclosed herein may also comprise at least one oxidation base chosen from the oxidation bases conventionally used for oxidation dyeing, and among which mention may be made of para-phenylenediamines, bis(phenyl)-alkylenediamines, para-aminophenols, ortho-aminophenols and heterocyclic bases, and the addition salts thereof with an acid or with an alkaline agent.

Among the para-phenylenediamines that may be mentioned are, for example, para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine and 4'-aminophenyl-1-(3-hydroxy)pyrrolidine, and the addition salts thereof with an acid or with an alkaline agent.

Among the para-phenylenediamines mentioned above, ones that may be mentioned are para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, and 2-β-acetylaminoethyloxy-para-phenylenediamine, and the addition salts thereof with an acid or with an alkaline agent.

Among the bis(phenyl)alkylenediamines that may be mentioned are, for example, N,N'-bis(β-hydroxyethyl)-N,N'-bis (4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis (β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl) ethylenediamine, 1,8-bis(2,5-diaminophenoxy)-3,5-dioxaoctane, and the addition salts thereof with an acid or with an alkaline agent.

Among the para-aminophenols that may be mentioned are, for example, para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, and the addition salts thereof with an acid or with an alkaline agent.

Among the ortho-aminophenols that may be mentioned are, for example, 2-aminophenol, 2-amino-5-methylphenol, 2-amino-6-methylphenol, 5-acetamido-2-aminophenol, and the addition salts thereof with an acid or with an alkaline agent.

Among the heterocyclic bases that may be mentioned are, for example, pyridine derivatives, pyrimidine derivatives, pyrazole derivatives, and the addition salts thereof with an acid or with an alkaline agent.

When it is used, the at least one oxidation base may be present in an amount ranging from 0.0005% to 12% by weight, such as from 0.005% to 6% by weight, relative to the total weight of the composition.

The composition may also comprise, combined with at least one oxidation base, at least one coupler so as to modify or to enrich with tints the shades obtained.

The at least one coupler that may be used may be chosen from couplers conventionally used in oxidation dyeing, and among which mention may be made of meta-phenylenediamines, meta-aminophenols, meta-diphenols, heterocyclic couplers, and the addition salts thereof with an acid or with an alkaline agent.

These couplers may, for example, be chosen from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-di-hydroxy-4-methylpyridine, 1H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole, 6-methylpyrazolo[1,5-a]benzimidazole, and the addition salts thereof with an acid or with an alkaline agent.

When it is present, the at least one coupler may be present in an amount ranging from 0.0001% to 10% by weight, such as from 0.005% to 5% by weight, relative to the total weight of the composition.

In general, the acid addition salts may be chosen from hydrochlorides, hydrobromides, sulfates, citrates, succinates, tartrates, tosylates, benzenesulfonates, lactates, and acetates.

The dye composition disclosed herein may also comprise at least one entity chosen from polymers and surfactants.

When the composition comprises at least one polymer, it may, for example, be chosen from associative and non-associative thickening polymers, conditioning polymers, and fixing polymers.

It is pointed out that associative polymers are hydrophilic polymers capable, in an aqueous medium, of reversibly combining together and/or with other molecules.

The chemical structure of the associative polymers may comprise at least one hydrophilic zone and at least one hydrophobic zone.

The associative polymers present in the composition disclosed herein may be nonionic, anionic, cationic, or amphoteric.

Among the associative polyurethane derivatives that may be mentioned are the anionic copolymers obtained by polymerization of:
  about 20% to 70% by weight of an α,β-monoethylenically unsaturated carboxylic acid,
  about 20% to 80% by weight of a non-surfactant α,β-monoethylenically unsaturated monomer, which is different from the previous monomer, and
  about 0.5% to 60% by weight of a nonionic monourethane, which is the product of reaction of a monohydroxylated surfactant with a monoethylenically unsaturated monoisocyanate.

Such polymers are, for example, described in European Patent No. EP 173 109, such as in Example 3. For example, this polymer may be a methacrylic acid/methyl acrylate/dimethyl meta-isopropenyl benzyl isocyanate terpolymer of ethoxylated behenyl alcohol (40 EO) as an aqueous 25% dispersion. This product is sold under the reference Viscophobe® DB1000 by the company Amerchol.

Cationic associative polyurethanes, the family of which has been described, for example, in French Patent Application No. FR 0 009 609, are also suitable for use.

The associative polyurethane derivatives disclosed herein may also be nonionic polyurethane polyethers. For example, the polymers may comprise in their chain both hydrophilic blocks which may be of polyoxyethylenated nature, and hydrophobic blocks that may be aliphatic chains alone and/or cycloaliphatic chains and/or aromatic chains.

In certain embodiments, these polyurethane polyethers comprise at least two hydrocarbon-based lipophilic chains, containing from 6 to 30 carbon atoms, separated by a hydrophilic block, the hydrocarbon-based chains optionally being pendent chains or chains at the end of a hydrophilic block. In certain embodiments, it is possible for at least one pendent chain to be provided. In addition, the at least one polymer may comprise a hydrocarbon-based chain at one or both ends of a hydrophilic block.

The polyurethane polyethers may be multiblock, such as in triblock form. The hydrophobic blocks may be at each end of the chain (for example: triblock copolymer containing a hydrophilic central block) or distributed both at the ends and in the chain (for example multiblock copolymer). These same polymers may also be chosen from graft polymers and starburst polymers.

The fatty-chain nonionic polyurethane polyethers may be triblock copolymers whose hydrophilic block is a polyoxyethylenated chain comprising from 50 to 1000 oxyethylene groups.

As examples of hydrophobic-chain nonionic polyurethane polyethers that may be used in accordance with certain embodiments, use may be made of Rheolate® 205 containing a urea function, sold by the company Rheox, Rheolate® 208, Rheolate® 204, Rheolate® 212, and Acrysol® RM 184.

Mention may also be made of the product Elfacos® T210 containing a $C_{12-14}$ alkyl chain and the product Elfacos® T212 containing a $C_{18}$ alkyl chain, from Akzo.

The product DW 1206B from Rohm & Haas containing a $C_{20}$ alkyl chain and a urethane linkage, sold at a solids content of 20% in water, may also be used.

It is also possible to use solutions and dispersions of these polymers, for example in water or in aqueous-alcoholic medium. Examples of such polymers that may be mentioned are Rheolate® 255, Rheolate® 278, and Rheolate® 244 sold by the company Rheox. The products DW 1206F and DW 1206J sold by the company Rohm & Haas may also be used.

The polyurethane polyethers that may be used according to certain embodiments disclosed herein may also be chosen from those described in the article by G. Formum, J. Bakke, and Fk. Hansen—Colloid Polym. Sci. 271, 380-389 (1993).

According to certain embodiments disclosed herein, it is possible to use a polyurethane polyether that may be obtained by polycondensation of at least three compounds comprising (i) at least one polyethylene glycol comprising from 150 to 180 mol of ethylene oxide, (ii) stearyl alcohol or decyl alcohol, and (iii) at least one diisocyanate.

Such polyurethane polyethers are sold by the company Rohm & Haas under the names Aculyn® 46 and Aculyn® 44 [Aculyn 46® is a polycondensate of polyethylene glycol containing 150 or 180 mol of ethylene oxide, of stearyl alcohol, and of methylenebis(4-cyclohexyl isocyanate) (SMDI), at 15% by weight in a matrix of maltodextrin (4%) and water (81%); Aculyn® 44 is a polycondensate of polyethylene glycol containing 150 or 180 mol of ethylene oxide, of decyl alcohol, and of methylenebis(4-cyclohexylisocyanate) (SMDI), at 35% by weight in a mixture of propylene glycol (39%) and water (26%)].

The composition may also comprise polymers derived from associative celluloses, such as at least one of the following:
  quaternized cationic celluloses modified with groups comprising at least one hydrophobic chain, such as alkyl, arylalkyl, and alkylaryl groups containing at least 8 carbon atoms; and
  quaternized cationic hydroxyethylcelluloses modified with groups comprising at least one hydrophobic chain, such as alkyl, arylalkyl, and alkylaryl groups containing at least 8 carbon atoms.

The alkyl radicals borne by the above quaternized celluloses and hydroxyethylcelluloses may contain from 8 to 30 carbon atoms. The aryl radicals may be chosen from phenyl, benzyl, naphthyl, and anthryl groups.

Examples of quaternized alkylhydroxyethylcelluloses containing $C_8$-$C_{30}$ hydrophobic chains that may be mentioned include the products Quatrisoft® LM 200, Quatrisoft® LM-X 529-18-A, Quatrisoft® LM-X 529-18B ($C_{12}$ alkyl), and Quatrisoft® LM-X 529-8 ($C_{18}$ alkyl) sold by the company Amerchol, and the products Crodacel QM, Crodacel QL ($C_{12}$ alkyl), and Crodacel QS ($C_{18}$ alkyl) sold by the company Croda.

nonionic cellulose derivatives such as hydroxyethyl celluloses modified with groups comprising at least one hydrophobic chain, such as alkyl, arylalkyl, and alkylaryl groups, and in which the alkyl groups may be of $C_8$-$C_{22}$, for instance the product Natrosol® Plus Grade 330 CS ($C_{16}$ alkyls) sold by the company Aqualon, and the product Bermocoll® EHM 100 sold by the company Berol Nobel, and cellulose derivatives modified with polyalkylene glycol alkylphenol ether groups, such as the product Amercell® Polymer HM-1500 sold by the company Amerchol.

As regards the associative polyvinyllactams, examples that may be mentioned include the polymers described in French Patent No. FR 0 101 106.

Mention may also be made of terpolymers comprising, on a weight basis, 40% to 95% of monomer (a), 0.1% to 55% of monomer (c), and 0.25% to 50% of monomer (b).

Such polymers are described, for example, in patent application WO 00/68282, the description of such polymers being incorporated by reference herein.

As poly(vinyllactam) polymers, vinylpyrrolidone/dimethylaminopropylmethacrylamide/dodecyldimethylmethacrylamidopropylammonium, tosylate terpolymers, vinylpyrrolidone/dimethylaminopropylmethacrylamide/cocoyldimethylmethacrylamidopropylammonium, tosylate terpolymers, vinylpyrrolidone/dimethylaminopropylmethacrylamide/laurylidimethylmethacrylamidopropylammonium, tosylate, and chloride terpolymers may be mentioned.

The associative polyvinyllactam derivatives disclosed herein may also be nonionic copolymers of vinylpyrrolidone and of hydrophobic monomers containing a hydrophobic chain, among which mention may be made, for example, of:

the products Antaron® V216 and Ganex® V216 (vinylpyrrolidone/hexadecene copolymer) sold by the company ISP, and the products Antaron® V220 and Ganex® V220 (vinylpyrrolidone/eicosene copolymer) sold by the company ISP.

Among the associative unsaturated polyacid derivatives that may be mentioned are those comprising at least one hydrophilic unit of unsaturated olefinic carboxylic acid type, and at least one hydrophobic unit of unsaturated carboxylic acid ($C_{10}$-$C_{30}$) alkyl ester type.

Anionic polymers of this type are disclosed and prepared, for example, according to U.S. Pat. Nos. 3,915,921 and 4,509,949.

In anionic associative polymers of this type, use may be made of polymers formed from a mixture of monomers comprising:
(i) essentially acrylic acid,
(ii) an alkyl(meth)acrylate containing from 12 to 22 carbon atoms, and
(iii) a crosslinking agent, which is a well-known copolymerizable polyethylenic unsaturated monomer, for instance diallyl phthalate, allyl(meth)acrylate, divinylbenzene, (poly)ethylene glycol dimethacrylate, and methylenebisacrylamide.

Among the anionic associative polymers of this type, ones that may be mentioned are those comprising from 95% to 60% by weight of acrylic acid (hydrophilic unit), 4% to 40% by weight of $C_{10}$-$C_{30}$ alkyl acrylate (hydrophobic unit), and 0% to 6% by weight of crosslinking polymerizable monomer, or alternatively those comprising from 98% to 96% by weight of acrylic acid (hydrophilic unit), 1% to 4% by weight of $C_{10}$-$C_{30}$ alkyl acrylate (hydrophobic unit), and 0.1% to 0.6% by weight of crosslinking polymerizable monomer such as those described above.

Among the above polymers, examples include the products sold by the company Goodrich under the trade names Pemulen® TR1, Pemulen® TR2, and Carbopol® 1382, such as Pemulen® TR1, and the product sold by the company SEPPIC under the name Coatex® SX.

Among the associative unsaturated polyacid derivatives that may also be mentioned are those comprising among their monomers an α,β-monoethylenically unsaturated carboxylic acid and an ester of an α,β-monoethylenically unsaturated carboxylic acid and of an oxyalkylenated fatty alcohol.

These compounds also may comprise as monomer an ester of an α,β-monoethylenically unsaturated carboxylic acid and of a $C_1$-$C_4$ alcohol.

An example of compounds of this type that may be mentioned is Aculyn® 22 sold by the company Rohm & Haas, which is a methacrylic acid/ethyl acrylate/oxyalkylenated stearyl methacrylate terpolymer.

As regards the non-associative thickening polymers, these polymers do not contain a $C_{10}$-$C_{30}$ fatty chain.

Among the non-associative thickening polymers, mention may be made of acrylic acid homopolymers crosslinked, for example, with an allylic ether of an alcohol of the sugar series, for instance the products sold under the names Carbopol® 980, 981, 954, 2984, and 5984 by the company Noveon and the products sold under the names Synthalen® M and Synthalen® K by the company 3 VSA.

Among the non-associative thickening polymers, mention may also be made of crosslinked 2-acrylamido-2-methylpropanesulfonic acid homopolymers, and crosslinked acrylamide copolymers thereof, which are partially or totally neutralized. The homopolymers described in European Patent Application No. EP 815 828, to which reference may be made in this respect, are, for example, suitable for use. Among the partially or totally neutralized crosslinked copolymers of 2-acrylamido-2-methylpropanesulfonic acid and of acrylamide, mention may be made of the product described in Example 1 of document EP 503 853, and reference may be made to the said document as regards these polymers. It should be noted that, when the compounds are neutralized, this may be performed by using a base such as sodium hydroxide, potassium hydroxide, and amines.

Ammonium, acrylate homopolymers and copolymers of ammonium acrylate and of acrylamide are also suitable for use as non-associative thickening polymers.

Among the ammonium acrylate homopolymers that may be mentioned is the product sold under the name Microsap® PAS 5193 by the company Hoechst. Among the copolymers of ammonium acrylate and of acrylamide that may be mentioned is the product sold under the name Bozepol C Nouveau and the product PAS 5193 sold by the company Hoechst. Reference may be made to patent documents FR 2 416 723, U.S. Pat. No. 2,798,053, and U.S. Pat. No. 2,923,692 as regards the description and preparation of such compounds.

Dimethylaminoethyl methacrylate homopolymers quaternized with methyl chloride and dimethylaminoethyl methacrylate copolymers quaternized with methyl chloride and acrylamide may also be used as non-associative thickening polymers.

Among the homopolymers of this family, mention may be made of the products sold under the names Salcare® 95 and Salcare® 96 by the company Ciba-Allied Colloids. Among the copolymers of this family, mention may be made of the product Salcare® SC92 sold by Ciba-Allied Colloids and the product PAS 5194 sold by Hoechst. These polymers are described and prepared, for example, in document EP 395 282, to which reference may be made.

Unmodified nonionic guar gums such as those sold under the name Vidogum GH 175 by the company Unipectine and under the name Jaguar® C by the company Meyhall are also suitable for use.

It is similarly possible to use nonionic guar gums modified with $C_1$-$C_6$ hydroxyalkyl groups (such as hydroxymethyl, hydroxyethyl, hydroxypropyl, and hydroxybutyl groups).

Such nonionic guar gums modified with hydroxyalkyl groups are sold, for example, under the trade names Jaguar® HP8, Jaguar® HP60, Jaguar® HP120, Jaguar® DC 293, and Jaguar® HP 105 by the company Meyhall and under the name Galactosol 4H4FD2 by the company Aqualon.

Also suitable for use are biopolysaccharide gums of microbial origin, for instance scleroglucan gum and xanthan gum; gums derived from plant exudates, such as gum arabic, ghatti gum, karaya gum, and gum tragacanth; hydroxypropyl- and carboxymethyl celluloses; pectins; and alginates. Such compounds are described, for example, in Robert L. Davidson's book entitled "Handbook of Water soluble gums and resins" published by the McGraw-Hill Book Company (1980).

The concentration of the at least one associative or non-associative thickening polymer in the dye composition may range from 0.01% to 10% by weight, such as from 0.1% to 5% by weight, relative to the total weight of the dye composition.

As indicated previously, the composition disclosed herein may comprise at least one conditioning polymer and/or at least one fixing polymer.

As used herein, the term "conditioning agent" means any agent whose function is to improve the cosmetic properties of keratin materials such as the hair, for example the softness, disentangling, feel, smoothness, and static electricity.

Conditioning polymers that are suitable are chosen from cationic polymers, cationic polyorganosiloxanes, and non-ionic polyorganosiloxanes.

As used herein, the term "cationic polymer" means any polymer containing cationic groups and/or groups that may be ionized into cationic groups.

These cationic polymers may be chosen from all those already known per se for their ability to improve the cosmetic properties of hair treated with detergent compositions. Mention may be made, for example, of those described in patent applications EP 0 337 354, FR 2 270 846, FR 2 383 660, FR 2 598 611, FR 2 470 596, and FR 2 519 863.

Cationic polymers that may be mentioned are chosen from those containing units comprising primary, secondary, tertiary, and/or quaternary amine groups which form part of the main macromolecular chain, or which are borne by side groups that are directly attached thereto.

Additional cationic polymers that may be mentioned are polymers of the polyamine, polyamino amide, and polyquaternary ammonium type. These are known products.

The polymers of the polyamine, polyamino amide, and polyquaternary ammonium type that may be used in accordance with certain embodiments are, for example, those described in French Patent Nos. 2 505 348 and 2 542 997. Among these polymers, mention may be made of:

(1) homopolymers and copolymers derived from at least one of acrylic esters, methacrylic esters, acrylic amides, and methacrylic amides containing an amine function, comprising at least one of the units of the following formulae:

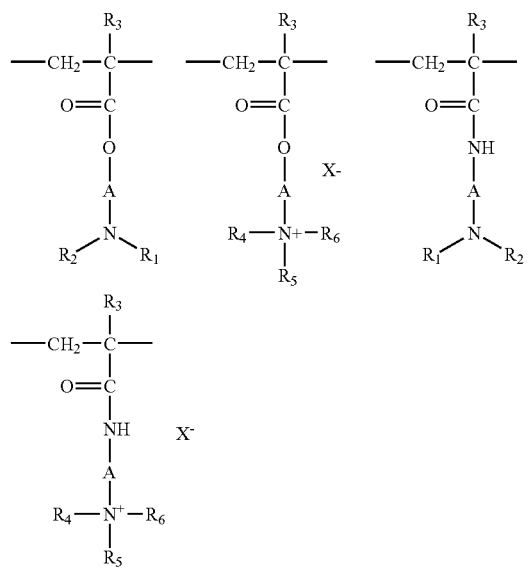

in which:

$R_3$, which may be identical or different, is chosen from hydrogen and $CH_3$ groups;

A, which may be identical or different, is chosen from linear or branched alkyl groups of 1 to 6 carbon atoms, such as 2 or 3 carbon atoms, and hydroxyalkyl groups of 1 to 4 carbon atoms;

$R_4$, $R_5$, and $R_6$, which may be identical or different, are chosen from alkyl groups containing from 1 to 18 carbon atoms and benzyl groups, for example alkyl groups containing from 1 to 6 carbon atoms;

$R_1$ and $R_2$, which may be identical or different, are chosen from hydrogen alkyl groups containing from 1 to 6 carbon atoms, such as methyl and ethyl groups;

$X^-$ is chosen from anions derived from mineral or organic acids, such as methosulfate anions and halides such as chloride and bromide.

The copolymers of family (1) can also comprise at least one unit derived from comonomers which may be chosen from the family of acrylamides, methacrylamides, diacetone acrylamides, acrylamides, and methacrylamides substituted on the nitrogen with $C_1$-$C_4$ lower alkyl groups, groups derived from at least one of acrylic acids, acrylic esters, methacrylic acids, methacrylic esters thereof, from vinyllactams such as vinylpyrrolidone and vinylcaprolactam, and from vinyl esters.

Among these copolymers of family (1) that may be mentioned are:

copolymers of acrylamide and of dimethylaminoethyl methacrylate quaternized with dimethyl sulfate or with a dimethyl halide, such as the product sold under the name Hercofloc® by the company Hercules, copolymers of acrylamide and of methacryloyloxyethyltrimethylammonium chloride described, for example, in European Patent Application EP A 080 976 and sold under the name Bina Quat P 100 by the company Ciba Geigy, copolymers of acrylamide and of methacryloyloxyethyltrimethylammonium methosulfate sold under the name Reten by the company Hercules, quaternized or non-quaternized vinylpyrrolidone/dialkylaminoalkyl acrylate and methacrylate copolymers, such as the products sold under the name Gafquat® by the company ISP, such as, for example, Gafquat® 734 and Gafquat® 755, and the products known as Copolymer 845, 958, and 937. These polymers are described in detail, for example, in French Patent Nos. 2 077 143 and 2 393 573, dimethylaminoethyl methacrylate/vinylcaprolactam/vinylpyrrolidone terpolymers, such as the product sold under the name Gaffix® VC 713 by the company ISP, vinylpyrrolidone/methacrylamidopropyldimethylamine copolymers sold for example under the name Styleze® CC 10 by ISP, and quaternized vinylpyrrolidone/dimethylaminopropylmethacrylamide copolymers such as the product sold under the name Gafquat® HS 100 by the company ISP.

(2) The cellulose ether derivatives comprising quaternary ammonium groups, which are described, for example, in French patent 1 492 597, such as the polymers sold under the names JR (JR 400, JR 125, JR 30M) and LR (LR 400, LR 30M) by the company Union Carbide Corporation. These polymers are also defined in the CTFA dictionary as hydroxyethylcellulose quaternary ammoniums that have reacted with an epoxide substituted with a trimethylammonium group.

(3) Cationic cellulose derivatives such as the copolymers of cellulose or cellulose derivatives grafted with a water-soluble quaternary ammonium monomer, described for example in U.S. Pat. No. 4,131,576, such as hydroxyalkylcelluloses, for instance hydroxymethyl-, hydroxyethyl- and hydroxypropylcelluloses grafted with at least one salt chosen from methacryloylethyltrimethylammonium, methacrylamidopropyltrimethylammonium, and dimethyldiallylammonium salts.

The commercial products corresponding to this definition include the products sold under the name Celquat® L 200 and Celquat® H 100 by the company National Starch.

(4) The cationic polysaccharides described in U.S. Pat. Nos. 3,589,578 and 4,031,307, such as guar gums containing trialkylammonium cationic groups may be mentioned. Use may also be made, for example, of guar gums modified with a salt (e.g. chloride) of 2,3-epoxypropyltrimethylammonium.

Such products are sold, for example, under the trade names Jaguar® C13S, Jaguar® C15, Jaguar® C17, and Jaguar® C162 by the company Meyhall.

(5) Polymers comprising piperazinyl units and divalent alkylene or hydroxyalkylene radicals containing straight or branched chains, optionally interrupted with at least one of oxygen, sulfur, and nitrogen atoms and/or with aromatic or heterocyclic rings, and also the oxidation and/or quaternization products of these polymers. Such polymers are described, for example, in French Patent Nos. 2 162 025 and 2 280 361.

(6) Water-soluble polyamino amides prepared, for example, by polycondensation of an acidic compound with a polyamine. These polyamino amides can be crosslinked with at least one of the following entities: epihalohydrins, diepoxides, dianhydrides, unsaturated dianhydrides, bis-unsaturated derivatives, bis-halohydrins, bis-azetidiniums, bis-haloacyidiamines, bis-alkyl halides, and oligomers resulting from the reaction of a difunctional compound which is reactive with at least one of the following entities: bis-halohydrins, bis-azetidinium, bis-haloacyidiamines, bis-alkyl halides, epihalohydrins, diepoxides, and bis-unsaturated derivatives. The crosslinking agent may be used in amounts ranging from 0.025 to 0.35 mol per amine group of the polyamino amide. These polyamino amides can be alkylated or, if they contain at least one tertiary amine function, they can be quaternized. Such polymers are described, for example, in French Patent Nos. 2 252 840 and 2 368 508.

(7) Polyamino amide derivatives resulting from the condensation of polyalkylene polyamines with polycarboxylic acids followed by alkylation with difunctional agents. Mention may be made, for example, of adipic acid/dialkylaminohydroxyalkyldialkylenetriamine polymers in which the alkyl group contains from 1 to 4 carbon atoms, for example the alkyl group is chosen from methyl, ethyl, and propyl groups, and the alkylene group contains from 1 to 4 carbon atoms, for example an ethylene group. Such polymers are described, for example in French Patent No. 1 583 363.

Among these derivatives, mention may be made of the adipic acid/dimethylaminohydroxypropyl/diethylenetriamine polymers sold under the name Cartaretine F, F4 or F8 by the company Sandoz.

(8) Polymers obtained by reaction of a polyalkylene polyamine containing two primary amine groups and at least one secondary amine group with a dicarboxylic acid chosen from diglycolic acid and saturated aliphatic dicarboxylic acids containing from 3 to 8 carbon atoms. The molar ratio between the polyalkylene polyamine and the dicarboxylic acid ranges from 0.8:1 to 1.4:1. The polyamino amide resulting therefrom is reacted with epichlorohydrin in a molar ratio of epichlorohydrin relative to the secondary amine group of the polyamino amide ranging from 0.5:1 to 1.8:1. Such polymers are described, for example, in U.S. Pat. Nos. 3,227,615 and 2,961,347.

Polymers of this type are sold, for example, under the name Hercosett® 57 by the company Hercules Inc. and under the name PD 170 or Delsette® 101 by the company Hercules in the case of the adipic acid/epoxypropyl/diethylenetriamine copolymer.

(9) Cyclopolymers of alkyldiallylamine and of dialkyldiallylammonium, such as the homopolymers and copolymers containing, as a main constituent of the chain, units corresponding to formula chosen from (Va) and (Vb):

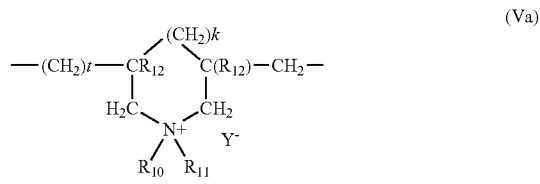

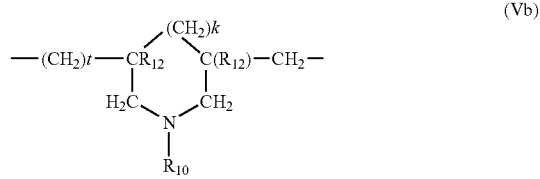

in which k and t are chosen from 0 and 1, the sum k plus t being equal to 1;

$R_{12}$ is chosen from hydrogen and methyl radicals;

$R_{10}$ and $R_{11}$, independently of each other, are chosen from alkyl groups containing from 1 to 22 carbon atoms, $C_{1-5}$ hydroxyalkyl groups, lower ($C_1$-$C_4$) amidoalkyl groups, or $R_{10}$ and $R_{11}$ can denote, together with the nitrogen atom to which they are attached, heterocyclic groups such as piperidyl and morpholinyl groups;

$Y^-$ is an anion such as bromide, chloride, acetate, borate, citrate, tartrate, bisulfate, bisulfite, sulfate, and phosphate.

These polymers are described, for example, in French Patent No. 2 080 759 and in its Certificate of Addition 2 190 406.

Among the polymers defined above, mention may be made of the dimethyldiallylammonium chloride homopolymer sold under the name Merquat® 100 by the company Calgon (and its homologues of low weight-average molecular mass) and copolymers of diallyldimethylammonium chloride and of acrylamide, sold under the name Merquat® 550.

(10) The quaternary diammonium polymers containing repeating units corresponding to formula (VI):

in which:

$R_{13}$, $R_{14}$, $R_{15}$, and $R_{16}$, which may be identical or different, are chosen from aliphatic, alicyclic, and arylaliphatic radicals containing from 1 to 20 carbon atoms and lower hydroxyalkylaliphatic radicals, or alternatively $R_{13}$, $R_{14}$, $R_{15}$, and $R_{16}$, together or separately, constitute, together with the nitrogen atoms to which they are attached, heterocycles optionally containing a second hetero atom other than nitrogen, or alternatively $R_{13}$, $R_{14}$, $R_{15}$, and $R_{16}$ are chosen from linear or branched $C_{1-6}$ alkyl radicals substituted with at least one group chosen from nitrile, ester, acyl, and amide groups and groups —CO—O—$R_{17}$-D and —CO—NH—$R_{17}$-D where $R_{17}$ is an alkylene group and D is a quaternary ammonium group;

$A_1$ and $B_1$ represent polymethylene groups containing from 2 to 20 carbon atoms, which groups may be linear or branched, saturated or unsaturated, and which may contain, linked to or intercalated in the main chain, at least one aromatic ring and/or at least one entity chosen from oxygen, sulfur, sulfoxide, sulfone, disulfide, amino, alkylamino, hydroxyl, quaternary ammonium, ureido, amide, and ester groups, and $X^-$ denotes an anion derived from an acid chosen from mineral acids and organic acids;

$A_1$, $R_{13}$, and $R_{15}$ can form, together with the two nitrogen atoms to which they are attached, a piperazine ring. In addition, if $A_1$ denotes a linear or branched, saturated or unsaturated alkylene or hydroxyalkylene radical, $B_1$ can also denote a group:

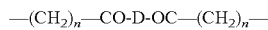

in which D is chosen from:

a) glycol residues of formula: —O-Z-O—, where Z is chosen from linear or branched hydrocarbon-based radicals and groups chosen from one of the following formulae:

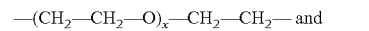

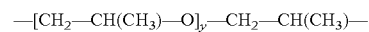

where x and y are chosen from integers ranging from 1 to 4, representing a defined and unique degree of polymerization or any number from 1 to 4 representing an average degree of polymerization;

b) bis-secondary diamine residues such as piperazine derivatives;

c) bis-primary diamine residues of formula —NH—Y—NH—, where Y is chosen from linear or branched hydrocarbon-based groups and divalent groups —$CH_2$—$CH_2$—S—S—$CH_2$—$CH_2$—; and d) ureylene groups of formula —NH—CO—NH—.

In certain embodiments, $X^-$ is an anion such as chloride and bromide.

These polymers generally have a number-average molecular mass ranging from 1,000 to 100,000.

Polymers of this type are described, for example, in French Patent Nos. 2 320 330, 2 270 846, 2 316 271, 2 336 434, and 2 413 907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945, and 4,027,020.

It is also possible to use polymers that comprise repeating units corresponding to the formula:

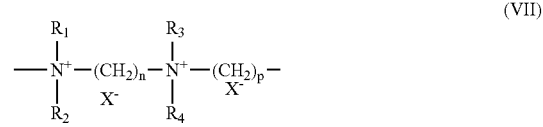

in which $R_1$, $R_2$, $R_3$, and $R_4$, which may be identical or different, are chosen from alkyl and hydroxyalkyl groups containing from 1 to 4 carbon atoms, n and p are chosen from integers ranging from 2 to 20, and $X^-$ is an anion derived from an acid chosen from mineral and organic acids.

One compound of formula (VII) that may be mentioned is the one wherein $R_1$, $R_2$, $R_3$, and $R_4$ represent a methyl group and n is 3, p is 6, and X is Cl, which is known as hexadimethrine chloride (CTFA).

(11) Polyquaternary ammonium polymers comprising units of formula (VIII):

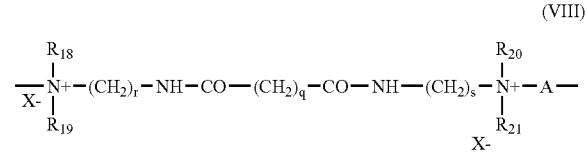

in which:

$R_{18}$, $R_{19}$, $R_{20}$, and $R_{21}$, which may be identical or different, are chosen from hydrogen and methyl, ethyl, propyl, β-hydroxyethyl, β-hydroxypropyl, and —$CH_2CH_2$ $(OCH_2CH_2)_pOH$ radicals, where p is chosen from 0 and integers ranging from 1 to 6, with the proviso that $R_{18}$, $R_{19}$, $R_{20}$, and $R_{21}$ do not simultaneously represent a hydrogen atom, r and s, which may be identical or different, are chosen from integers ranging from 1 to 6, q is chosen from 0 and integers ranging from 1 to 34, $X^-$ denotes an anion such as a halide, A is chosen from dihalide radicals and —$CH_2$—$CH_2$—O—$CH_2$—$CH_2$—.

Such compounds are described, for example, in European Patent Application No. EP-A-122 324.

Among these products, mention may be made, for example, of Mirapol® A 15, Mirapol® AD1, Mirapol® AZ1, and Mirapol® 175 sold by the company Miranol.

(12) Quaternary polymers of vinylpyrrolidone and of vinylimidazole, such as, for example, the products sold under the names Luviquat® FC 905, FC 550, and FC 370 by the company BASF. Mention may also be made of copolymers of vinylpyrrolidone and of methylvinylimidazolium chloride.

(13) Polyamines such as the product Polyquart® H sold by Henkel under the reference name Polyethylene Glycol (15) Tallow Polyamine in the CTFA dictionary.

(14) Crosslinked or non-crosslinked methacryloyloxy $(C_{1-4})$alkyltri$(C_{1-4})$alkylammonium salt polymers such as the polymers obtained by homopolymerization of dimethylaminoethyl methacrylate quaternized with methyl chloride, and by copolymerization of acrylamide with dimethylaminoethyl methacrylate quaternized with methyl chloride, the homo- or copolymerization being followed by crosslinking with a compound containing olefinic unsaturation, such as methylenebisacrylamide. An acrylamide/methacryloyloxyethyltrimethylammonium chloride crosslinked copolymer (20/80 by weight) in the form of a dispersion containing 50% by weight of the said copolymer in mineral oil may also be used. This dispersion is sold under the name Salcare® SC 92 by the company Allied Colloids. A crosslinked homopolymer of methacryloyloxyethyltrimethylammonium chloride containing about 50% by weight of the homopolymer in mineral oil or in a liquid ester may also be used. These dispersions are sold under the names Salcare® SC 95 and Salcare® SC 96 by the company Allied Colloids.

Other cationic polymers which can be used in the context of embodiments disclosed herein are cationic proteins and cationic protein hydrolysates, polyalkyleneimines, such as polyethyleneimines, polymers containing vinylpyridine and/or vinylpyridinium units, condensates of polyamines and of epichlorohydrin, quaternary polyureylenes, and cationic chitin derivatives.

The amino or non-amino polyorganosiloxanes (and organosiloxanes and silicones), which may be non-volatile, may also be used as conditioning agent. They may be in a form chosen from oils, waxes, resins, and gums.

Mention may also be made of polyalkylsiloxanes, polyarylsiloxanes, polyalkylarylsiloxanes, silicone gums, silicone resins, and polyorganosiloxanes modified with organic functional groups, and also mixtures thereof.

These silicones may be chosen from polyalkylsiloxanes, among which mention may be made of polydimethylsiloxanes containing trimethylsilyl end groups having a viscosity ranging from $5 \times 10^{-6}$ to 2.5 $m^2/s$ at 25° C., such as from $1 \times 10^{-5}$ to 1 $m^2/s$. The viscosity of the silicones is measured, for example, at 25° C. according to ASTM standard 445 Appendix C.

Among these polyalkylsiloxanes, mention may be made, in a non-limiting manner, of the following commercial products:

the Silbione® oils of the 47 and 70 047 series and the Mirasil® oils sold by Rhodia Chimie, such as, for example, the oil 70 047 V 500 000;

the oils of the Mirasil® series sold by the company Rhodia Chimie;

the oils of the 200 series from the company Dow Corning, such as DC200 with a viscosity of 60,000 cSt ($mm^2/s$);

the Viscasil® oils from General Electric and certain oils of the SF series (SF 96, SF 18) from General Electric.

Mention may also be made of polydimethylsiloxanes containing dimethylsilanol end groups (Dimethiconol according to the CTFA name) such as the oils of the 48 series from the company Rhodia Chimie; and also the products sold under the names Abil® Wax 9800 and 9801 by the company Goldschmidt, which are poly($C_1$-$C_{20}$)alkylsiloxanes.

The polyalkylarylsiloxanes may be chosen from linear and/or branched polydimethylmethylphenylsiloxanes and polydimethyldiphenylsiloxanes with a viscosity ranging from $1 \times 10^{-5}$ to $5 \times 10^{-2}$ $m^2/s$ at 25° C.

Among these polyalkylarylsiloxanes, mention may be made, by way of example, of the products sold under the following names:

the Silbione® oils of the 70 641 series from Rhodia Chimie;

the oils of the Rhodorsil® 70 633 and 763 series from Rhodia Chimie;

the oil Dow Corning 556 Cosmetic Grade Fluid from Dow Corning;

the silicones of the PK series from Bayer, such as the product PK20;

the silicones of the PN and PH series from Bayer, such as the products PN1000 and PH1000;

certain oils of the SF series from General Electric, such as SF 1023, SF 1154, SF 1250, and SF 1265.

The silicone gums that can be used in accordance with certain embodiments disclosed herein include polydiorganosiloxanes with high number-average molecular masses ranging from 200,000 to 1,000,000, used alone or as a mixture in a solvent. This solvent can be chosen from at least one of volatile silicones, polydimethylsiloxane (PDMS) oils, polyphenylmethylsiloxane (PPMS) oils, isoparaffins, polyisobutylenes, methylene chloride, pentane, dodecane, and tridecane.

Mention may also be made of the following products of polydimethylsiloxane type: polydimethylsiloxane/methylvinylsiloxane gums, polydimethylsiloxane/diphenylsiloxane, polydimethylsiloxane/phenylmethylsiloxane, and polydimethylsiloxane/diphenylsiloxane/methylvinylsiloxane gums.

Products that can be used in accordance with certain embodiments disclosed herein include mixtures such as:

mixtures formed from a polydimethylsiloxane hydroxylated at the chain end (referred to as dimethiconol according to the nomenclature in the CTFA dictionary) and from a cyclic polydimethylsiloxane (referred to as cyclomethicone according to the nomenclature in the CTFA dictionary), such as the product Q2 1401 sold by the company Dow Corning;

mixtures formed from a polydimethylsiloxane gum with a cyclic silicone, such as the product SF 1214 Silicone Fluid from the company General Electric. This product is an SF 30 gum corresponding to a dimethicone, having a number-average molecular weight of 500,000, dissolved in the oil SF 1202 Silicone Fluid corresponding to decamethylcyclopentasiloxane;

mixtures of two PDMSs with different viscosities, for example mixtures of a PDMS gum and a PDMS oil, such as the product SF 1236 from the company General Electric. The product SF 1236 is a mixture of an SE 30 gum defined above, having a viscosity of 20 m²/s, and an SF 96 oil, with a viscosity of $5\times10^{-6}$ m²/s. This product may contain 15% SE 30 gum and 85% SF 96 oil.

The organopolysiloxane resins that can be used in accordance with certain embodiments disclosed herein are crosslinked siloxane systems containing the following units: $R_2SiO_{2/2}$, $R_3SiO_{1/2}$, $RSiO_{3/2}$ and $SiO_{4/2}$ in which R is chosen from hydrocarbon-based groups containing 1 to 16 carbon atoms and phenyl groups. Among these products, those that may be mentioned include the ones in which R is chosen from $C_1$-$C_4$ lower alkyl radicals, such as methyl and phenyl radicals.

Among these resins, mention may be made of the product sold under the name Dow Corning 593 and those sold under the names Silicone Fluid SS 4230 and SS 4267 by the company General Electric, which are silicones of dimethyl/trimethyl siloxane structure.

Mention may also be made of the trimethyl siloxysilicate type resins, for example those sold under the names X22-4914, X21-5034, and X21-5037 by the company Shin-Etsu.

The organomodified silicones that can be used in accordance with certain embodiments disclosed herein are silicones as defined above and comprising in their structure at least one organofunctional group attached via a hydrocarbon-based radical. These organofunctional compounds are other than amino groups.

Among the organomodified silicones other than those chosen from formulae (I) and (II), mention may be made of polyorganosiloxanes comprising:

polyethyleneoxy and/or polypropyleneoxy groups optionally comprising $C_6$-$C_{24}$ alkyl groups, such as the products known as dimethicone copolyol sold by the company Dow Corning under the name DC 1248 and the $(C_{12})$alkylmethicone copolyol sold by the company Dow Corning under the name Q2 5200;

thiol groups such as the products sold under the names GP 72 A and GP 71 from Genesee;

alkoxylated groups such as the product sold under the name Silicone Copolymer F-755 by SWS Silicones and Abil® Wax 2428, 2434, and 2440 by the company Goldschmidt;

hydroxylated groups such as the polyorganosiloxanes containing a hydroxyalkyl function, described, for example, in French Patent Application No. FR A 85/16334;

acyloxyalkyl groups such as, for example, the polyorganosiloxanes described in U.S. Pat. No. 4,957,732;

anionic carboxylic groups, such as, for example, in the products described in European Patent No. EP 186 507 from the company Chisso Corporation, and anionic alkylcarboxylic groups, such as those present in the product X-22-3701 E from the company Shin-Etsu; 2-hydroxyalkyl sulfonate; and 2-hydroxyalkyl thiosulfate such as the products sold by the company Goldschmidt under the names Abil® S201 and Abil® S255.

According to certain embodiments disclosed herein, it is also possible to use silicones comprising a polysiloxane portion and a portion comprising a non-silicone organic chain, one of the two portions constituting the main chain of the polymer, the other being grafted onto the said main chain. These polymers are described, for example, in patent applications EP A 412 704, EP A 412 707, EP A 640 105, WO 95/00578, EP A 582 152, and WO 93/23009 and U.S. Pat. Nos. 4,693,935, 4,728,571, and 4,972,037. These polymers may be anionic or nonionic.

Other examples of grafted silicone polymers include polydimethylsiloxanes (PDMS) onto which are grafted, via a linking unit of thiopropylene type, mixed polymer units of the poly(meth)acrylic acid type and of the polyalkyl (meth)acrylate type, and polydimethylsiloxanes (PDMS) onto which are grafted, via a linking unit of thiopropylene type, polymer units of the polyisobutyl(meth)acrylate type.

It should be noted that the silicones may also be used in a form chosen from emulsions, nanoemulsions, and microemulsions.

As used herein, the term "fixing polymers" means any polymer for giving or maintaining a shape on a head of hair.

In certain embodiments, the at least one fixing polymer that may be used is chosen from at least one of anionic, amphoteric, and nonionic polymers.

The at least one fixing polymer may be soluble in the cosmetically acceptable medium or insoluble in this same medium and, in this case, used in the form of dispersions of solid or liquid polymer particles (latices or pseudolatices).

The anionic fixing polymers generally used are polymers comprising groups derived from at least one of carboxylic acid, sulfonic acid, and phosphoric acid and have a number-average molecular mass approximately ranging from 500 to 5,000,000.

The carboxylic groups are provided by unsaturated monocarboxylic or dicarboxylic acid monomers such as those corresponding to the formula:

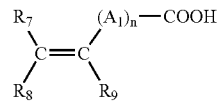

in which n is chosen from integers ranging from 0 to 10, $A_1$ denotes a methylene group, optionally connected to the carbon atom of the unsaturated group, or to the neighboring methylene group when n is greater than 1, via a hetero atom such as oxygen and sulfur, $R_7$ is chosen from hydrogen, phenyl groups, and benzyl groups, $R_8$ is chosen from hydrogen, lower alkyl groups, and carboxyl groups, and $R_9$ is chosen from hydrogen, lower alkyl groups, —$CH_2$—COOH, phenyl groups, and benzyl groups.

In the abovementioned formula, lower alkyl groups may be chosen from groups having 1 to 4 carbon atoms, such as methyl and ethyl groups.

The anionic fixing polymers containing carboxylic groups that may be mentioned are:

A) acrylic or methacrylic acid homo- or copolymers, and salts thereof, such as the products sold under the names Versicol E and K by the company Allied Colloid and Ultrahold® by the company BASF, the copolymers of acrylic acid and of acrylamide, and the sodium salts of polyhydroxycarboxylic acids.

B) copolymers of acrylic or methacrylic acid with a monoethylenic monomer such as ethylene, styrene, vinyl esters, acrylic acid esters, and methacrylic acid esters, optionally grafted onto a polyalkylene glycol such as polyethylene glycol and optionally crosslinked. Such polymers are described, for example, in French Patent No. 1 222 944 and German Patent Application No. 2 330 956, the copolymers of this type comprising an optionally N-alkylated and/or hydroxyalkylated acrylamide unit in their chain as described, for example, in Luxembourg Patent Application Nos. 75370 and 75371. Mention may also be made of copolymers of acrylic acid and of $C_1$-$C_4$ alkyl methacrylate and terpolymers of vinylpyrrolidone, of acrylic acid and of methacrylate of $C_1$-$C_{20}$ alkyl, for example of lauryl, such as the product sold by the company ISP under the name Acrylidone® LM and methacrylic acid/ethyl acrylate/tert-butyl acrylate terpolymers such as the product sold under the name Luvimer® 100 P by the company BASF.

C) crotonic acid copolymers, such as those comprising vinyl acetate and/or propionate units in their chain and optionally other monomers such as monomers chosen from allylic esters, methallylic esters, vinyl ethers and vinyl esters of a linear or branched saturated carboxylic acid with a long hydrocarbon chain such as those containing at least 5 carbon atoms, it being possible for these polymers optionally to be grafted or crosslinked, and vinyl, allylic, and methallylic ester monomers of an α- or β-cyclic carboxylic acid. Such polymers are described, inter alia, in French Patent Nos. 1 222 944, 1 580 545, 2 265 782, 2 265 781, 1 564 110, and 2 439 798. A commercial product falling into this class is the resin 28-29-30 sold by the company National Starch.

D) copolymers derived from $C_4$-$C_8$ monounsaturated carboxylic acids and/or anhydrides chosen from:

copolymers comprising (i) at least one entity chosen from maleic, fumaric, and itaconic acids and maleic, fumaric, and itaconic anhydrides and (ii) at least one monomer chosen from vinyl esters, vinyl ethers, vinyl halides, phenylvinyl derivatives, and acrylic acid and its esters, the anhydride functions of these copolymers optionally being monoesterified or monoamidated. Such polymers are described, for example, in U.S. Pat. Nos. 2,047,398, 2,723,248, and 2,102,113 and British Patent No. GB 839 805. Commercial products include, for example, those sold under the names Gantrez® AN and ES by the company ISP.

copolymers comprising (i) at least one unit chosen from maleic, citraconic, and itaconic anhydride units and (ii) at least one monomer chosen from allylic and methallylic esters optionally comprising at least one of acrylamide, methacrylamide, α-olefin, acrylic ester, and methacrylic ester, acrylic acid, methacrylic acid, and vinylpyrrolidone groups in their chain, the anhydride functions of these copolymers optionally being monoesterified or monoamidated.

These polymers are described, for example, in French Patent Nos. 2 350 384 and 2 357 241.

E) Polyacrylamides comprising carboxylate groups.

The polymers comprising sulfonic groups are polymers comprising a unit chosen from vinylsulfonic, styrenesulfonic, naphthalenesulfonic, and acrylamidoalkylsulfonic units.

These polymers can be chosen, for example, from:

polyvinylsulfonic acid salts having a molecular mass approximately between ranging from 1,000 to 100,000, as well as the copolymers with an unsaturated comonomer such as acrylic acids, methacrylic acids, and their esters, as well as acrylamide and its derivatives, vinyl ethers, and vinylpyrrolidone;

polystyrenesulfonic acid salts such as the sodium salts that are sold for example under the name Flexan® 130 by National Starch. These compounds are described, for example, in French Patent No. FR 2 198 719;

polyacrylamidesulfonic acid salts, such as those mentioned in U.S. Pat. No. 4,128,631, such as polyacrylamidoethylpropanesulfonic acid.

According to embodiments disclosed herein, among the anionic fixing polymers mentioned above, the ones that may be mentioned include acrylic acid copolymers, such as the acrylic acid/ethyl acrylate/N-tert-butylacrylamide terpolymers sold under the name Ultrahold® Strong by the company BASF, copolymers derived from crotonic acid, such as vinyl acetate/vinyl tert-butylbenzoate/crotonic acid terpolymers and the crotonic acid/vinyl acetate/vinyl neododecanoate terpolymers sold under the name Resin 28-29-30 by the company National Starch, polymers derived from maleic, fumaric and itaconic acids and anhydrides with vinyl esters, vinyl ethers, vinyl halides, phenylvinyl derivatives, and acrylic acid and esters thereof, such as the methyl vinyl ether/monoesterified maleic anhydride copolymers sold, for example, under the name Gantrez® by the company ISP, the copolymers of methacrylic acid and of methyl methacrylate sold under the name Eudragit® L by the company Rohm Pharma, the copolymers of methacrylic acid and of ethyl acrylate sold under the name Luvimer® MAEX and MAE by the company BASF, and the vinyl acetate/crotonic acid copolymers and the vinyl acetate/crotonic acid copolymers grafted with polyethylene glycol sold under the name Aristoflex® A by the company BASF.

Among the anionic fixing polymers disclosed above, ones that may be mentioned are chosen from the methyl vinyl ether/monoesterified maleic anhydride copolymers sold under the name Gantrez® ES 425 by the company ISP, the acrylic acid/ethyl acrylate/N-tert-butylacrylamide terpolymers sold under the name Ultrahold® Strong by the company BASF, the copolymers of methacrylic acid and of methyl methacrylate sold under the name Eudragit® L by the company Rohm Pharma, the vinyl acetate/vinyl tert-butylbenzoate/crotonic acid terpolymers and the crotonic acid/vinyl acetate/vinyl neododecanoate terpolymers sold under the name Resin 28-29-30 by the company National Starch, the copolymers of methacrylic acid and of ethyl acrylate sold under the name Luvimer® MAEX and MAE by the company BASF, and the vinylpyrrolidone/acrylic acid/lauryl methacrylate terpolymers sold under the name Acrylidone® LM by the company ISP.

The amphoteric fixing polymers that can be used in accordance with embodiments disclosed herein can be chosen from polymers comprising units B and C distributed randomly in the polymer chain, in which B denotes a unit derived from a monomer comprising at least one basic nitrogen atom and C denotes a unit derived from an acid monomer comprising at least one group chosen from carboxylic groups and sulfonic groups, or alternatively B and C can denote groups derived from aleast one of carboxybetaine and sulfobetaine zwitterionic monomers;

B and C can also denote a cationic polymer chain comprising primary, secondary, tertiary, or quaternary amine groups, in which at least one of the amine groups bears a group chosen from carboxylic groups and sulfonic group connected via a hydrocarbon group or alternatively B and C form part of a chain of a polymer containing an α,β-dicarboxylic ethylene unit in which one of the carboxylic groups has been made to react with a polyamine comprising at least one primary or secondary amine group.

The amphoteric fixing polymers corresponding to the definition given above that may be mentioned are chosen from the following polymers:

(1) polymers resulting from the copolymerization of a monomer derived from a vinyl compound bearing a carboxylic group such as, for example, acrylic acid, methacrylic acid, maleic acid, α-chloroacrylic acid, and a basic monomer derived from a substituted vinyl compound containing at least one basic atom, such as, for example, dialkylaminoalkyl methacrylate and acrylate, dialkylaminoalkylmethacrylamides and -acrylamides. Such compounds are described, for example, in U.S. Pat. No. 3,836,537.

(2) polymers comprising units derived from:
   a) at least one monomer chosen from acrylamides and methacrylamides substituted on the nitrogen atom with an alkyl group,
   b) at least one acidic comonomer containing at least one reactive carboxylic group, and
   c) at least one basic comonomer such as esters containing primary, secondary, tertiary, and quaternary amine substituents of acrylic and methacrylic acids and the product of quaternization of dimethylaminoethyl methacrylate with dimethyl or diethyl sulfate.

The N-substituted acrylamides and methacrylamides that may be mentioned according certain embodiments disclosed herein are compounds in which the alkyl groups contain from 2 to 12 carbon atoms, such as N-ethylacrylamide, N-tert-butyl-acrylamide, N-tert-octylacrylamide, N-octylacrylamide, N-decylacrylamide, N-dodecylacrylamide, and the corresponding methacrylamides.

The acidic comonomers may be chosen from acrylic acid, methacrylic acid, crotonic acid, itaconic acid, maleic acid, fumaric acid, and alkyl monoesters, having 1 to 4 carbon atoms, of at least one of maleic acid, malic anhydride, fumaric acid, and fumaric anhydride.

Examples of basic comonomers include aminoethyl, butylaminoethyl, N,N'-dimethylaminoethyl, and N-tert-butylaminoethyl methacrylates.

The copolymers whose CTFA (4th edition, 1991) name is octylacrylamide/acrylates/butylaminoethyl methacrylate copolymer, such as the products sold under the name Amphomer® and Lovocryl® 47 by the company National Starch, may also be mentioned.

(3) crosslinked and acylated polyamino amides partially or totally derived from polyamino amides of the general formula:

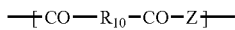

in which $R_{10}$ is chosen from divalent groups derived from at least of saturated dicarboxylic acids, mono- and dicarboxylic aliphatic acids containing an ethylenic double bond, esters of a lower alkanol, having 1 to 6 carbon atoms, of these acids, and groups derived from the addition of any one of said acids to a bis(primary) or bis (secondary) amine, and Z is chosen from groups derived from at least one of bis(primary), mono- and bis(secondary) polyalkylene-polyamine and may, for example, represent:

a) in an amount ranging from from 60 to 100 mol %, the group:

where x is 2 and p is chosen from 2 and 3, or alternatively x is 3 and p is 2,
this group being derived from at least one of diethylenetriamine, triethylenetetraamine, and dipropylenetriamine;

b) in an amount ranging from 0 to 40 mol %, the group (IIIa) above in which x is 2 and p is 1 and which is derived from ethylenediamine, or the group derived from piperazine:

c) in an amount ranging from 0 to 20 mol %, the —NH (CH$_2$)$_6$—NH— group being derived from hexamethylenediamine, these polyamino amides being crosslinked by addition reaction of a difunctional crosslinking agent chosen from epihalohydrins, diepoxides, dianhydrides, and bis-unsaturated derivatives, using from 0.025 to 0.35 mol of crosslinking agent per amine group of the polyamino amide and acylated by the action of at least one of acrylic acid, chloroacetic acid, alkane sultones, and salts thereof.

The saturated carboxylic acids may be chosen from acids having 6 to 10 carbon atoms, such as adipic acid, 2,2,4-trimethyladipic acid, 2,4,4-trimethyladipic acid, terephthalic acid, and acids containing an ethylenic double bond such as, for example, acrylic acid, methacrylic acid, and itaconic acid.

The alkane sultones used in the acylation may, for example, be chosen from propane sultone and butane sultone. The salts of the acylating agents may be chosen from the sodium and potassium salts.

(4) polymers comprising zwitterionic units of formula:

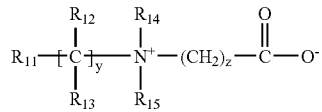

in which $R_1$ is chosen from polymerizable unsaturated groups such as acrylate, methacrylate, acrylamide, and methacrylamide groups, y and z are chosen from integers ranging from 1 to 3, $R_{12}$ and $R_{13}$ are chosen from hydrogen, methyl groups, ethyl groups, and propyl groups, $R_{14}$ and $R_{15}$ are chosen from hydrogen and alkyl groups such that the sum of the carbon atoms in $R_{14}$ and $R_{15}$ does not exceed 10.

The polymers comprising such units can also comprise units derived from non-zwitterionic monomers such as dimethylaminoethyl acrylate, dimethylaminoethyl methacrylate, diethylaminoethyl acrylate, diethylaminoethyl methacrylate, alkyl acrylates, alkyl methacrylates, acrylamides, methacrylamides, and vinyl acetate.

By way of example, mention may be made of the copolymers of methyl methacrylate/methyl dimethylcarboxymethylammonioethyl methacrylate.

(5) polymers derived from chitosan comprising monomer units corresponding to the following formulae:

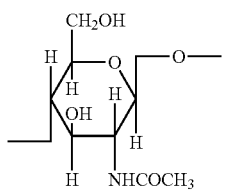 (I)

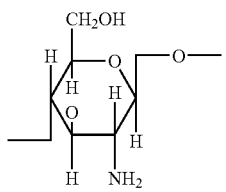 (II)

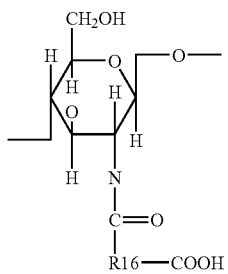 (III)

the unit (I) being present in an amount ranging from 0 to 30%, the unit (II) present in an amount ranging from 5 to 50%, and the unit (III) present in an amount ranging from 30% to 90%, it being understood that, in this unit (III), $R_{16}$ represents a group of formula:

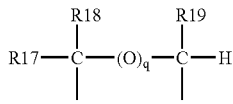

in which, if q is 0, $R_{17}$, $R_{18}$, and $R_{19}$, which may be identical or different, each are chosen from hydrogen, methyl residues, hydroxyl residues, acetoxy residues, amino residues, \monoalkylamine residues, dialkylamine residues that are optionally interrupted by at least one nitrogen atom and/or optionally substituted with at least one group chosen from amine, hydroxyl, carboxyl, alkylthio, and sulfonic groups, and alkylthio residues in which the alkyl group bears an amino residue, at least one of the groups $R_{17}$, $R_{18}$, and $R_{19}$ being, in this case, hydrogen;

or, if q is 1, $R_{17}$, $R_{18}$, and $R_{19}$ each represent hydrogen, as well as the salts formed by these compounds with bases or acids.

(6) polymers corresponding to the general formula (V) that are described, for example, in French Patent No. 1 400 366:

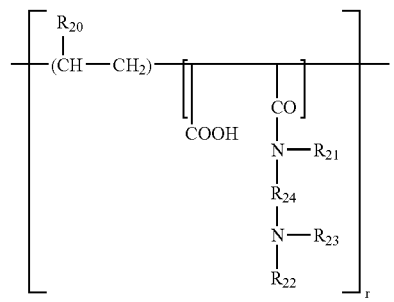

in which $R_{20}$ is chosen from hydrogen, $CH_3O$ groups, $CH_3CH_2O$ groups, and phenyl groups, $R_{21}$ being chosen from hydrogen and lower alkyl groups such as methyl and ethyl, $R_{22}$ being chosen from hydrogen and $C_1$-$C_6$ lower alkyl groups such as methyl and ethyl, $R_{23}$ being chosen from $C_1$-$C_6$ lower alkyl groups such as methyl and ethyl and groups corresponding to the formula: —$R_{24}$—$N(R_{22})_2$, and $R_{24}$ being chosen from —$CH_2$—$CH_2$—, —$CH_2$—$CH_2$—$CH_2$—, and —$CH_2$—$CH(CH_3)$— groups, $R_{22}$ having the meanings mentioned above.

(7) polymers derived from the N-carboxyalkylation of chitosan, such as N-carboxymethylchitosan and N-carboxybutylchitosan.

(8) amphoteric polymers of the type -D-X-D-X— chosen from:

a) polymers obtained by the action of chloroacetic acid or sodium chloroacetate on compounds comprising at least one unit of formula:

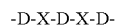 (VI)

where D denotes a group

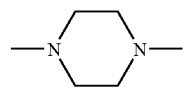

and X is chosen from the symbols E and E'. E and E', which may be identical or different, are chosen from divalent groups that are alkylene groups with a straight or branched chain containing up to 7 carbon atoms in the main chain, which is unsubstituted or substituted with hydroxyl groups and which can comprise, in addition to the oxygen, nitrogen, and sulfur atoms, 1 to 3 aromatic and/or heterocyclic rings; the oxygen, nitrogen, and sulfur atoms being present in a form chosen from ether, thioether, sulfoxide, sulfone, sulfonium, alkylamine, alkenylamine, hydroxyl, benzylamine, amine oxide, quaternary ammonium, amide, imide, alcohol, ester, and urethane groups;

b) polymers of formula:

 (VI')

where D denotes a group

and X is chosen from the symbols E and E' and at least once E'; E having the meaning given above and E' is a divalent group that is an alkylene group with a straight or branched chain having up to 7 carbon atoms in the main chain, which is unsubstituted or substituted with at least one hydroxyl group and containing at least one nitrogen atom, the nitrogen atom being substituted with an alkyl chain that is optionally interrupted by an oxygen atom and necessarily comprising at least one carboxyl function or at least one hydroxyl function and betainized by reaction with at least one of chloroacetic acid and sodium chloroacetate.

(9) ($C_1$-$C_5$)alkyl vinyl ether/maleic anhydride copolymers partially modified by semiamidation with an N,N-dialkylaminoalkylamine such as N,N-dimethylaminopropylamine or by semiesterification with an N,N-dialkylaminoalkanol. These copolymers can also comprise other vinyl comonomers such as vinylcaprolactam.

Among the amphoteric fixing polymers mentioned above, the ones that may be mentioned according to certain embodiments disclosed herein are those of the family (3), such as the copolymers whose CTFA name is octylacrylamide/acrylates/butylaminoethyl methacrylate copolymer, such as the products sold under the names Amphomer®, Amphomer® LV 71, and Lovocryl® 47 by the company National Starch and those of the family (4) such as methyl methacrylate/methyl dimethylcarboxymethylammonioethylmethacrylate copolymers.

The nonionic fixing polymers that may be used according to certain embodiments disclosed herein are chosen, for example, from:
  polyalkyloxazolines;
  vinyl acetate homopolymers;
  copolymers of vinyl acetate and of acrylic ester;
  copolymers of vinyl acetate and of ethylene;
  copolymers of vinyl acetate and of maleic ester, for example of dibutyl maleate;
  copolymers of acrylic esters, for instance copolymers of alkyl acrylates and of alkyl methacrylates, such as the products sold by the company Rohm & Haas under the names Primal® AC-261 K and Eudragit® NE 30 D, by the company BASF under the name 8845, and by the company Hoechst under the name Appretan N9212;
  copolymers of acrylonitrile and of a nonionic monomer chosen, for example, from butadiene and alkyl(meth)acrylates; mention may be made of the products sold under the name CJ 0601 B by the company Rohm & Haas;
  styrene homopolymers;
  copolymers of styrene and of an alkyl(meth)acrylate, such as the products Mowilith® LDM 6911, Mowilith® DM 611, and Mowilith® LDM 6070 sold by the company Hoechst, and the products Rhodopas® SD 215 and Rhodopas® DS 910 sold by the company Rhodia Chimie;
  copolymers of styrene, of alkyl methacrylate, and of alkyl acrylate;
  copolymers of styrene and of butadiene;
  copolymers of styrene, of butadiene, and of vinylpyridine;
  copolymers of alkyl acrylate and of urethane;
  polyamides; and
  vinyllactam homopolymers and copolymers.

The alkyl groups in the nonionic polymers mentioned above may, for example, have from 1 to 6 carbon atoms.

According to embodiments disclosed herein, the nonionic fixing polymers containing vinyllactam units may be those described in U.S. Pat. Nos. 3,770,683, 3,929,735, 4,521,504, 5,158,762, and 5,506,315 and in patent applications WO 94/121148, WO 96/06592, and WO 96/10593. They may be in a form chosen from pulverulent solution form, and suspension form.

The homopolymers or copolymers containing vinyllactam units comprise units of formula (IX):

in which n is independently chosen from 3, 4, and 5.

The number-average molar mass of the polymers containing vinyllactam units is generally greater than about 5,000, such as ranging from about 10,000 to 1,000,000 or from about 10,000 to 100,000.

Among these fixing polymers, mention may be made of polyvinylpyrrolidones such as those sold under the name Luviskol® K30 by the company BASF; polyvinylcaprolactams such as those sold under the name Luviskol® PLUS by the company BASF; poly(vinyl-pyrrolidone/vinyl acetate) copolymers such as those sold under the name PVPVA® S630L by the company ISP, Luviskol® VA 73, VA 64, VA 55, VA 37, and VA 28 by the company BASF; and poly(vinylpyrrolidone/vinyl acetate/vinyl propionate) terpolymers, for instance those sold under the name Luviskol® VAP 343 by the company BASF.

The fixing polymers disclosed herein may also be chosen from optionally silicone-based nonionic or anionic polyurethanes.

The amount of conditioning polymer or of fixing polymer present may ranges from 0.01% to 20% by weight relative to the total weight of the dye composition, such as from 0.1% to 5% by weight relative to the total weight of the dye composition.

When the composition comprises at least one surfactant, this surfactant is chosen from nonionic, anionic, cationic, amphoteric, and zwitterionic species.

By way of example of anionic surfactants that can be used, alone or as mixtures, mention may be made of salts (for example alkali metal salts and alkaline-earth metal salts, such as sodium salts, magnesium salts, ammonium salts, amine salts, and amino alcohol salts) of the following compounds: alkyl sulfates, alkyl ether sulfates, alkylamido ether sulfates, alkylarylpolyether sulfates, monoglyceride sulfates; alkyl sulfonates, alkyl phosphates, alkylamide sulfonates, alkylaryl sulfonates, α-olefin sulfonates, paraffin sulfonates; ($C_6$-$C_{24}$)alkyl sulfosuccinates, ($C_6$-$C_{24}$)alkyl ether sulfosuccinates, ($C_6$-$C_{24}$)alkylamide sulfosuccinates; ($C_6$-$C_{24}$)alkyl sulfoacetates; ($C_6$-$C_{24}$)acyl sarcosinates; and ($C_6$-$C_{24}$)acyl glutamates.

It is also possible to use ($C_6$-$C_{24}$)alkylpolyglycoside carboxylic esters such as alkylglucoside citrates, alkylpolyglycoside tartrates, alkylpolyglycoside sulfosuccinates, alkylsulfosuccinamates; acyl isethionates, and N-acyl taurates, the alkyl and/or acyl radical of all of these different compounds optionally containing from 12 to 20 carbon atoms and the aryl radical optionally being chosen from phenyl groups and benzyl groups.

Among the anionic surfactants which can also be used, mention may also be made of fatty acid salts such as oleic, ricinoleic, palmitic, and stearic acid salts, coconut oil acid, hydrogenated coconut oil acid; and acyl lactylates in which the acyl radical is a $C_8$-$C_{20}$ radical.

It is also possible to use at least one of alkyl D-galactoside uronic acids and their salts, polyoxyalkylenated ($C_6$-$C_{24}$) alkyl ether carboxylic acids, polyoxyalkylenated ($C_6$-$C_{24}$) alkylaryl ether carboxylic acids, polyoxyalkylenated ($C_6$-$C_{24}$)alkylamido ether carboxylic acids and their salts, such as those containing from 2 to 50 alkylene oxide groups, such as ethylene oxide groups.

Examples of nonionic surfactants that may be mentioned, inter alia, include $C_8$-$C_{18}$ polyethoxylated and polypropoxylated, alkylphenols, alpha-diols and alcohols, the number of ethylene oxide and/or propylene oxide groups ranging from 2 to 50.

Mention may also be made of copolymers of ethylene oxide and of propylene oxide, condensates of ethylene oxide and of propylene oxide with fatty alcohols; polyethoxylated fatty amides preferably having from 2 to 30 mol of ethylene oxide, polyglycerolated fatty amides containing on average 1 to 5, for example 1.5 to 4, glycerol groups; polyethoxylated fatty amines optionally having from 2 to 30 mol of ethylene oxide; oxyethylenated fatty acid esters of sorbitan having from 2 to 30 mol of ethylene oxide; fatty acid esters of sucrose, fatty acid esters of polyethylene glycol, alkylpolyglycosides, N-alkylglucamine derivatives, and amine oxides such as ($C_{10}$-$C_{14}$)alkylamine oxides and N-acylaminopropylmorpholine oxides.

As regards the amphoteric or zwitterionic surfactants, mention may be made, without being limited thereto, of aliphatic secondary and tertiary amine derivatives in which the aliphatic radical is a linear or branched chain containing 8 to 18 carbon atoms and containing at least one water-solubilizing anionic group (for example carboxylate, sulfonate, sulfate, phosphate, and phosphonate groups); mention may also be made of ($C_8$-$C_{20}$)alkylbetaines, sulfobetaines, ($C_8$-$C_{20}$)alkylamido($C_1$-$C_6$)alkylbetaines, and ($C_8$-$C_{20}$)alkylamido($C_1$-$C_6$)alkylsulfobetaines.

Among the amine derivatives, mention may be made of the products sold under the name Miranol®, as described in U.S. Pat. Nos. 2,528,378 and 2,781,354 and classified in the CTFA dictionary, 3rd edition, 1982, under the names amphocarboxyglycinates and amphocarboxypropionates, with the respective structures:

in which:
$R_2$ is chosen from alkyl radicals of an acid $R_2$—COOH present in hydrolyzed coconut oil, heptyl radicals, nonyl radicals, and undecyl radicals, $R_3$ denotes a beta-hydroxyethyl group, and $R_4$ denotes a carboxymethyl group; and

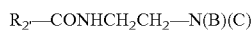

in which:
B represents —$CH_2CH_2OX'$, C represents —$(CH_2)_z$—Y', wherein z is chosen from 1 and 2,
X' is chosen from —$CH_2CH_2$—COOH groups and hydrogen,
Y' is chosen from —COOH and —$CH_2$—CHOH—$SO_3$H radicals,
$R_2$' is chosen from alkyl radicals of an acid $R_9$—COOH present in coconut oil or in hydrolysed linseed oil, and alkyl radicals, such as $C_7$, $C_9$, $C_{11}$, and $C_{13}$ alkyl radicals, $C_{17}$ alkyl radicals and its iso forms, and unsaturated $C_{17}$ radicals.

These compounds are classified in the CTFA dictionary, 5th edition, 1993, under the names disodium cocoamphodiacetate, disodium lauroamphodiacetate, disodium caproamphodiacetate, disodium capryloamphodiacetate, disodium cocoamphodipropionate, disodium lauroamphodipropionate, disodium caproamphodipropionate, disodium caproamphodipropionate, lauroamphodipropionic acid, cocoamphodipropionic acid, and disodium cocoamphocarboxyethyl hydroxypropyl sulfonate.

By way of further example, mention may be made of cocoamphodiacetate sold under the trade name Miranol® C2M Concentrate by the company Rhodia Chimie.

Among the cationic surfactants that may be mentioned are optionally polyoxyalkylenated primary, secondary, and tertiary fatty amine salts; quaternary ammonium salts such as tetraalkylammonium, alkylamidoalkyltrialkylammonium, trialkylbenzylammonium, trialkylhydroxyalkylammonium and alkylpyridinium chlorides and bromides; imidazoline derivatives; and amine oxides of cationic nature; and monoquaternary and diquaternary esters known as esterquat.

The amount of the at least one surfactant, when it is present, may, for example, be in an amount ranging from 0.001% to 30% by weight, such as from 0.05% to 30% by weight, relative to the total weight of the dye composition.

The composition may also comprise at least one additive that is common in the field, for example, mineral thickeners, antioxidants, penetrants, sequestrants, fragrances, buffers, dispersants, conditioning agents, for instance, cations, volatile or non-volatile, modified or unmodified silicones, film-forming agents, ceramides, preserving agents, stabilizers, and opacifiers.

Needless to say, a person skilled in the art will take care to select this at least one optional additional compound such that the advantageous properties intrinsically associated with the composition disclosed herein are not, or are not substantially, adversely affected by the envisaged addition.

The pH of the composition disclosed herein generally ranges from 3 to 12, such as from 4 to 10.

It may be adjusted to the desired value by means of acidifying and basifying agents.

Examples of acidifying agents that may be mentioned include acids chosen from mineral acids and organic acids, for instance hydrochloric acid, orthophosphoric acid, sulfuric acid, carboxylic acids, for instance acetic acid, tartaric acid, citric acid, and lactic acid, and sulfonic acids.

Examples of basifying agents that may be mentioned include aqueous ammonia, alkaline carbonates, alkanolamines such as monoethanolamine, diethanolamine and triethanolamine and derivatives thereof, sodium hydroxide, potassium hydroxide, and the compounds of formula (A) below:

(A)

in which W is a propylene residue optionally substituted with a group chosen from hydroxyl groups and $C_1$-$C_6$ alkyl radicals; $R_1$, $R_2$, $R_3$, and $R_4$, which may be identical or different, are chosen from hydrogen atoms, $C_1$-$C_6$ alkyl radicals, and $C_1$-$C_6$ hydroxyalkyl radicals.

The composition disclosed herein may be in various forms, such as in a form chosen from liquids, shampoos, creams, gels, mousses, and any other suitable form.

One embodiment disclosed herein is also a ready-to-use composition comprising the dye composition comprising at least one compound chosen from formulae (1) and (2).

As used herein, a ready-to-use composition corresponds to a composition intended to be applied immediately to keratin fibers, i.e. it may be stored as such or may result from the extemporaneous mixing of at least two compositions before use.

According to one embodiment disclosed herein, the dye composition described is a composition that may be applied directly to keratin materials. For example, this composition may be free of an oxidizing agent.

Such a composition may be suitable when the composition comprises the at least one compound chosen from porphyrin compounds and phthalocyanin compounds, optionally and at least one additional direct dye, and when it is not desired to obtain a lightening effect on the fibers.

According to another embodiment disclosed herein, the ready-to-use composition comprises, besides the at least one compound chosen from porphyrin compounds and phthalocyanin compounds, at least one oxidizing agent. In this case, the composition may also optionally comprise at least one additional direct dye, at least one oxidation base, and/or at least one coupler. It may also comprise at least one surfactant and/or at least one polymer.

The oxidizing agent may be chosen, for example, from hydrogen peroxide, urea peroxide, alkali metal bromates, persalts such as perborates and persulfates, and enzymes such as peroxidases and two-electron or four-electron oxidoreductases. The use of hydrogen peroxide and/or enzymes may be mentioned.

The ready-to-use composition in accordance with this embodiment may be obtained by mixing before use at least one dye composition comprising the at least one direct dye (porphyrin and/or phthalocyanin and additional direct dyes, if they are present) and/or dye precursors (base/coupler), which may or may not be combined in at least one composition, with a composition comprising at least one oxidizing agent (oxidizing composition).

The amount of the at least one oxidizing agent present may range from 1% to 40% by weight, relative to the total weight of the ready-to-use composition, such as from 1% to 20% by weight, relative to the total weight of the ready-to-use composition.

Generally, the oxidizing composition used is an aqueous composition and may be in a form chosen from solutions and emulsions.

In certain embodiments, the composition free of oxidizing agent may be mixed with about 0.5 to 10 weight equivalents of the oxidizing composition.

The pH of the ready-to-use composition may range from 3 to 12, such as from 4 to 10.

The pH of the ready-to-use composition may be adjusted using basifying and/or acidifying agents chosen, for example, from those mentioned previously.

As indicated previously, the present disclosure furthermore relates to a process for dyeing keratin fibers using the composition disclosed herein.

According to one embodiment, the process comprises applying the composition in the absence of an oxidizing agent, to wet or dry keratin materials, such as fibers, with or without final rinsing of the composition.

According to another embodiment, the process comprises applying the composition disclosed herein, in the presence of at least one oxidizing agent, to wet or dry keratin materials, and then in leaving it to act for a time sufficient to obtain the desired coloration.

The applied composition may be the ready-to-use composition, i.e. a composition obtained by extemporaneous mixing of at least one dye composition comprising the dyes with a composition comprising at least one oxidizing agent.

The process according to this embodiment may also comprise applying a dye composition free of an oxidizing agent and then a composition comprising at least one oxidizing agent, or vice versa, with or without intermediate rinsing.

The time required to develop the coloration may range from about a few seconds to 60 minutes, such as from about 1 to 40 minutes.

The temperature required to develop the coloration may range from room temperature (15 to 25° C.) to 250° C., such as from room temperature to 180° C. or from room temperature to 60° C.

Once the time required to develop the coloration has elapsed, the composition may be removed. This may be carried out in a conventional manner, either by performing at least one rinsing operation and/or by performing at least one washing operation. Finally, the keratin materials may be dried or left to dry.

When the ready-to-use composition does not comprise at least one oxidation dye precursor (base and/or coupler) but only, as dye, at least one direct dye chosen from formulae (1) and (2) and optionally at least one different additional direct dye, the process may be performed under "lightening" conditions.

When the composition is applied in the presence of at least one oxidizing agent, the process may comprise a preliminary step comprising separately storing, on the one hand, at least one composition comprising, in a medium that is suitable for dyeing human keratin fibers, the at least one compound chosen from formulae (1) and (2), optionally at least one additional direct dye, optionally at least one oxidation base and optionally at least one coupler, and, on the other hand, a composition comprising, in a medium that is suitable for dyeing human keratin fibers, at least one oxidizing agent, and then in mixing them together at the time of use, before applying this mixture to the wet or dry keratin materials, for a time that is sufficient to develop the desired coloration, after which the keratin materials are, after optionally having rinsed them, optionally washed with shampoo, rinsed again, and dried.

The time required to develop the coloration may range from about a few seconds to 60 minutes, such as from about 1 to 40 minutes.

The temperature required to develop the coloration may range from room temperature (15 to 25° C.) to 250° C., such as from room temperature to 180° C. or from room temperature to 60° C.

Another embodiment disclosed herein is a multi-compartment device for dyeing keratin materials, such as fibers, comprising at least one compartment with, in a medium that is suitable for dyeing human keratin fibers, the at least one compound chosen from non-metallic cationic porphyrin and phthalocyanin compounds and metallic cationic porphyrin and phthalocyanin compounds comprising as the metal element at least one metal or metal ion chosen from column IA and IIA of the Periodic Table of the Elements, zinc, and silicon, optionally at least one additional direct dye, optionally at least one oxidation base and optionally at least one coupler; these compounds being present in at least one composition, which may or may not be combined, and, on the other hand, a compartment with a composition comprising, in a medium that is suitable for dyeing human keratin fibers, at least one oxidizing agent.

This device may be equipped with a means for applying the desired mixture to the fibers, such as the devices described in French Patent No. FR 2 586 913.

Furthermore, disclosed herein is a cationic phthalocyanin compound having the following formula:

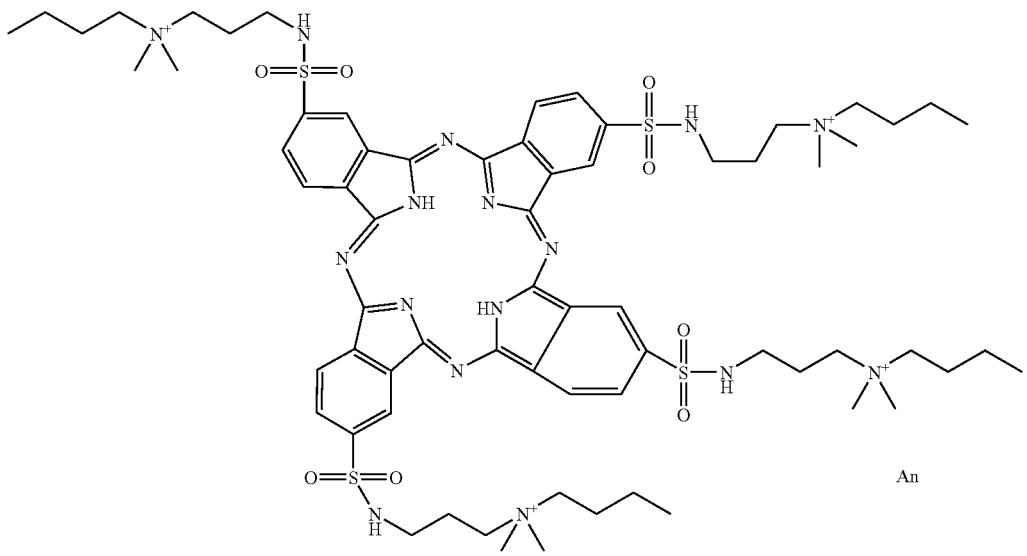

An being as defined previously.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, unless otherwise indicated the numerical values set forth in the specific examples are reported as precisely as possible. Any numerical value, however, inherently contain certain errors necessarily resulting from the standard deviation found in their respective testing measurements.

Concrete but non-limiting examples of the present disclosure will now be presented.

EXAMPLES

Example 1

Dye 1: 5,10, 15-20-tetrakis(1-methyl-4-pyridino)porphyrin tetra(p-toluenesulfonate)

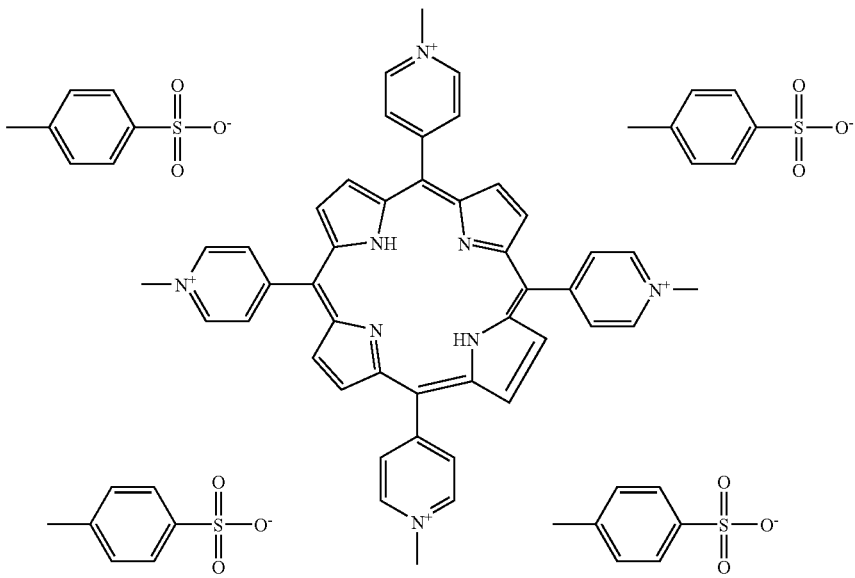

Composition A below was prepared:

| Compound | Concentration (g %) |
|---|---|
| (50/50 C8/C10)alkyl polyglucoside (2) as a buffered aqueous 60% solution | 10 |
| Benzyl alcohol | 10 |
| Polyethylene glycol 400 (8 EO) | 12 |
| Dye 1 | 0.5 |
| 20.6% aqueous ammonia | 13 |
| Water | qs 100 |

Uptake of the Dye

Formula A was mixed with commercial 40-volumes aqueous hydrogen peroxide solution (weight-for-weight mixture) and was then applied to locks of permanent-waved hair containing 90% white hairs (formula/lock mass ratio: 10/1), after a leave-in time of 20 minutes at room temperature (T=25° C.±3° C.), the locks were rinsed and shampooed once (Elsève multivitamines), the color uptakes were measured using a calorimeter (CM2002 calorimeter, illuminant D65-10° SCI).

As shown by the table below, the dye showed good uptake on the hair.

| | Color |
|---|---|
| Undyed lock | Grey |
| Dye 1 | Strong brown |

Fastness Relative to Repeated Shampooing

Formula A was mixed with commercial 40-volumes aqueous hydrogen peroxide solution (weight-for-weight mixture) and was then applied to locks of grey hair containing 90% white hairs, sensitized by bleaching. The formula/lock mass ratio was 10/1, after a leave-in time of 20 minutes at room temperature (T=25° C.±3° C.), the locks were rinsed and dried and the calorimetric values were measured, the locks were then shampooed six times, after which the colorimetric values were again measured, the calorimetric values measured after shampooing six times were compared with the calorimetric values before shampooing.

The results show that the color obtained on sensitized hair (brown) shows very good fastness relative to repeated shampooing.

| Dye 1 | |
|---|---|
| | ΔE * ab (before/after shampooing) |
| Dye 1 before shampooing Dye 1 after shampooing six times | 1.19 |

Example 2

Dye 2: formula $C_{66}H_{102}N_{18}O_8S_4I_4$

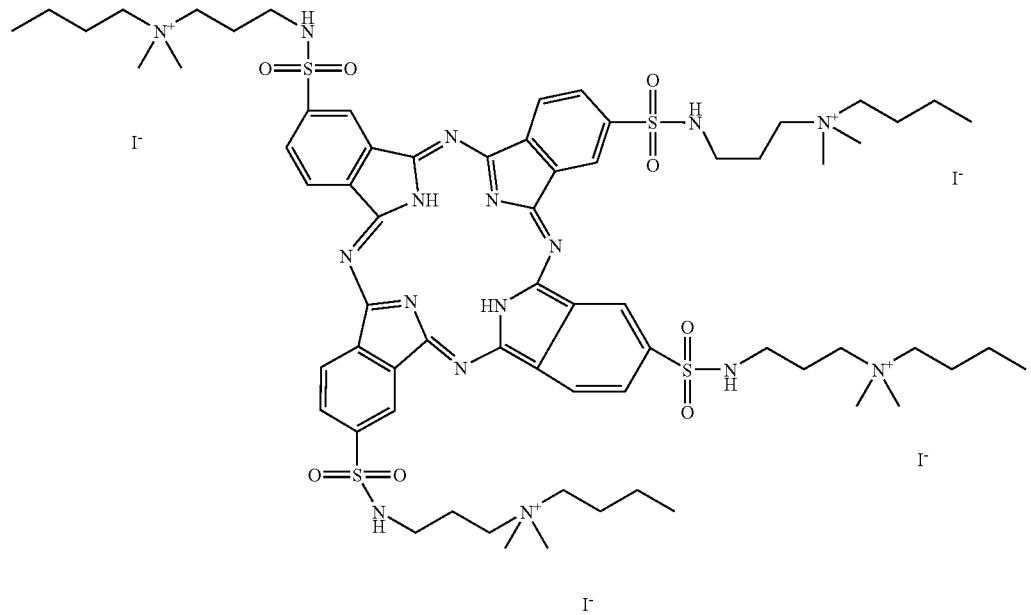

Composition B below was prepared:

| Compound | Concentration (g %) |
|---|---|
| (50/50 C8/C10)alkyl polyglucoside (2) as a buffered aqueous 60% solution | 10 |
| Benzyl alcohol | 10 |
| Polyethylene glycol 400 (8 EO) | 12 |
| Dye 2 | 0.5 |
| 20.6% aqueous ammonia | 13 |
| Water | qs 100 |

Uptake of the Dye

Formula B was mixed with commercial 40-volumes aqueous hydrogen peroxide solution (weight-for-weight mixture) and was then applied to locks of permanent-waved hair containing 90% white hairs (formula/lock mass ratio: 10/1), after a leave-in time of 20 minutes at room temperature (T=25° C.±3° C.), the locks were rinsed and shampooed once (Elsève multivitamines), the color uptakes were measured using a calorimeter (CM2002 calorimeter, illuminant D65-10° SCI).

As shown by the table below, the dye showed good uptake on the hair.

|  | Color |
| --- | --- |
| Undyed lock | Grey |
| Dye 2 | Strong turquoise |

Fastness Relative to Repeated Shampooing

Formula B was mixed with commercial 40-volumes aqueous hydrogen peroxide solution (weight-for-weight mixture) and was then applied to locks of permanent-waved grey hair containing 90% white hairs, sensitized by bleaching. The formula/lock mass ratio was 10/1, after a leave-in time of 20 minutes at room temperature (T=25° C.±3° C.), the locks were rinsed and dried and the colorimetric values were measured, the locks were then shampooed six times, after which the colorimetric values were again measured, the calorimetric values measured after shampooing six times were compared with the colorimetric values before shampooing.

The results show that the color obtained on sensitized hair (turquoise) showed very good fastness relative to repeated shampooing.

| Dye 2 | ΔE * ab (before/after shampooing) |
| --- | --- |
| Dye 2 before shampooing Dye 21 after shampooing six times | 1.68 |

Light Stability of Dye 2

Formula B was mixed with commercial 40-volumes aqueous hydrogen peroxide solution (weight-for-weight mixture) and was then applied to locks of permanent-waved grey (PWG) hair containing 90% white hairs (formula/lock mass ratio: 10/1), after a leave-in time of 20 minutes at room temperature (T=25° C.±3° C.), the locks were rinsed and dried and the colorimetric values were measured, half of each lock was then placed in the Suntest for 18 hours (intensity equivalent to exposure for 3 weeks at the height of August), the unexposed half serving as control, the colorimetric values measured after exposure to light were compared with the values before exposure.

As shown by the table below, dye 2 showed very good light stability.

|  | ΔE * ab (before/after shampooing) |
| --- | --- |
| Dye 2 before light test Dye 2 after light test | 2.28 |

Example 3

Dye 3 zinc 5,10,15,20-tetrakis(4-(N-methylpyridinium)-21H,23H-porphyrin tetratosylate

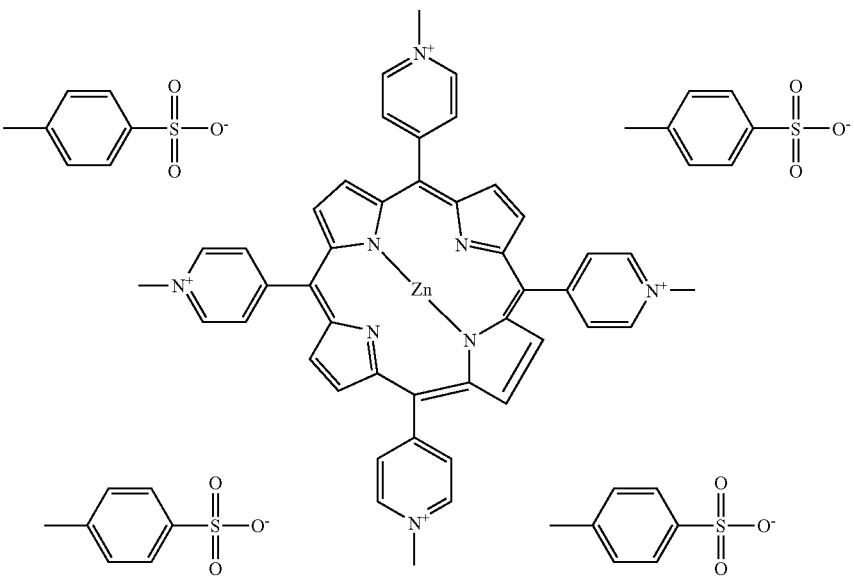

Composition C below was prepared:

| Constituent | g % |
|---|---|
| Oleyl alcohol polyglycerolated with 2 mol of glycerol | 4 |
| Oleyl alcohol polyglycerolated with 4 mol of glycerol | 5.69 AM |
| Oleic acid | 3 |
| Oleylamine containing 2 mol of ethylene oxide, sold under the trade name Ethomeen 012 by the company Akzo | 7 |
| Diethylaminopropyl laurylaminosuccinamate, sodium salt, containing 55% AM | 3.0 AM |
| Oleyl alcohol | 5 |
| Oleic acid diethanolamide | 12 |
| Ethyl alcohol | 7 |
| Propylene glycol | 3.5 |
| Dipropylene glycol | 0.5 |
| Propylene glycol monomethyl ether | 9 |
| Antioxidant/sequestrant | qs |
| Ammonium acetate | 0.8 |
| Sodium metabisulfite as an aqueous 35% solution | 0.455 |
| Dye 3 | 3.71 |
| 20% aqueous ammonia | 10 |
| Demineralized water qs | 100 g |

Uptake of the Dye

Formula C was mixed with commercial 20-volumes aqueous hydrogen peroxide solution (weight-for-weight mixture) and was then applied to locks of bleached hair containing 90% white hairs (formula/lock mass ratio: 10/1), after a leave-in time of 20 minutes at room temperature (T=25° C.±3° C.), the locks were rinsed and shampooed once (Elsève multivitamines), the color uptakes were measured using a calorimeter (CM2002 calorimeter, illuminant D65-10° SCI).

As shown by the table below, the dye showed good uptake on the hair.

| | Color |
|---|---|
| Undyed lock | Grey |
| Dye 3 | Strong green |

Light Stability of Dye 3

The lock dyed via the protocol described above (see the "dye uptake" paragraph) was placed in the Suntest for 18 hours (intensity equivalent to exposure for 3 weeks at the height of August), the calorimetric values measured after exposure to light were compared with the values before exposure.

As shown by the table below, dye 3 showed good light stability.

| | ΔE * ab (before/after shampooing) |
|---|---|
| Dye 3 before light test | 4.51 |
| Dye 3 after light test | |

What is claimed is:

1. A method of dyeing human keratin materials comprising applying to the human keratin materials at least one direct dye comprising at least one non-metallic or metallic cationic compound chosen from porphyrin compounds and phthalocyanin compounds, wherein the metal element is at least one metal or metal ion chosen from columns IA and IIA of the Periodic Table of the Elements, zinc, and silicon.

2. The method according to claim 1, wherein the human keratin materials are fibers.

3. The method according to claim 1, wherein the at least one non-metallic or metallic cationic compound chosen from porphyrin compounds and phthalocyanin compounds corresponds to formula (1) below, and the tautomeric forms thereof, bearing at least one cationic charge:

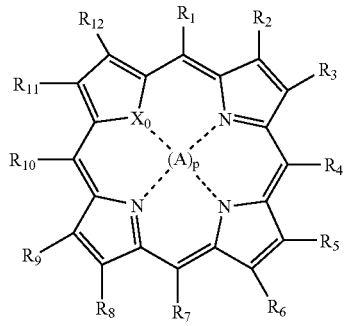

An⁻ in which:

the radicals $R_1$ to $R_{12}$, which may be identical or different, are chosen from at least one of the following:

hydrogen;

linear or branched $C_1$-$C_{30}$ alkyl radicals; linear or branched $C_2$-$C_{30}$ alkenyl radicals;

linear or branched $C_2$-$C_{30}$ alkynyl radicals;

wherein the alkyl, alkenyl, and alkynyl radicals are optionally substituted with at least one monovalent group chosen from at least one of the following groups:

hydroxyl groups;

amino groups;

amino groups substituted with at least one linear or branched $C_1$-$C_{10}$ alkyl radical, which may be identical or different, optionally bearing at least one group chosen from hydroxyl groups and linear or branched $C_1$-$C_{10}$ alkoxy groups;

ammonium groups substituted with one, two, or three linear or branched $C_1$-$C_{10}$ alkyl radicals, which may be identical or different, optionally bearing at least one group chosen from hydroxyl groups and linear or branched $C_1$-$C_{10}$ alkoxy groups;

hydrogenocarbonyl (—COH) groups; and optionally substituted 5- or 6-membered heterocycles, comprising at least one hetero atom, optionally bearing at least one cationic charge, wherein the heterocycle is optionally fused with an aromatic nucleus;

wherein the alkyl, alkenyl, and alkynyl radicals are optionally interrupted with at least one divalent group chosen from the following groups:

oxygen;

amino groups;

amino groups substituted with at least one linear or branched $C_1$-$C_{10}$ alkyl radicals, optionally bearing at least one group chosen from hydroxyl groups and linear or branched $C_1$-$C_{10}$ alkoxy groups;

ammonium groups substituted with one or two linear or branched $C_1$-$C_{10}$ alkyl radicals, which may be identical or different, optionally bearing at least one group chosen from hydroxyl groups and linear or branched $C_1$-$C_{10}$ alkoxy groups;

carbonyl (—CO—) groups; and
optionally substituted 5- or 6-membered heterocycles, comprising at least one hetero atom, optionally bearing at least one cationic charge;
optionally substituted $C_6$-$C_{30}$ aryl radicals; optionally substituted ($C_1$-$C_{30}$)alkyl($C_6$-$C_{30}$)aryl radicals; optionally substituted ($C_6$-$C_{30}$)aryl($C_1$-$C_{30}$)alkyl radicals;
hydroxyl groups;
optionally substituted linear or branched $C_1$-$C_{30}$ alkoxy radicals;
amino radicals; amino radicals bearing at least one optionally substituted linear or branched $C_1$-$C_{30}$ alkyl radical;
radicals —$SO_2$—$NH_2$, —$SO_2$NH-alkyl, and —NH—$SO_2$-alkyl, in which the alkyl radical is an optionally substituted linear or branched $C_1$-$C_{30}$ alkyl; and
optionally cationic, optionally aromatic, 5- or 6-membered heterocyclic radicals, comprising at least one nitrogen atom, and optionally at least one other hetero atom, which may be identical or different, wherein the said heterocyclic radical is optionally substituted;
wherein at least one of the radicals $R_1$ to $R_{12}$ bears at least one cationic charge;
$X_0$ is chosen from nitrogen and oxygen;
A is a metal or metal ion chosen from columns IA and IIA of the Periodic Table of the Elements, zinc, and silicon;
p is chosen from 0, 1, and 2 depending on the nature of the element A; and
An is at least one cosmetically acceptable anion that compensates the total cationic charge of the compound.

4. The method according to claim 3, wherein the at least one hetero atom is chosen from oxygen and nitrogen.

5. The method according to claim 3, wherein aromatic nucleus is 6-membered.

6. The method according to claim 3, wherein the metal or metal ion chosen from columns IA and IIA of the Periodic Table of the Elements is chosen from sodium, potassium, magnesium, and calcium.

7. The method according to claim 1, wherein the at least one non-metallic or metallic cationic compound chosen from porphyrin compounds and phthalocyanin compounds corresponds to formula (2) below, and the tautomeric forms thereof, bearing at least one cationic charge:

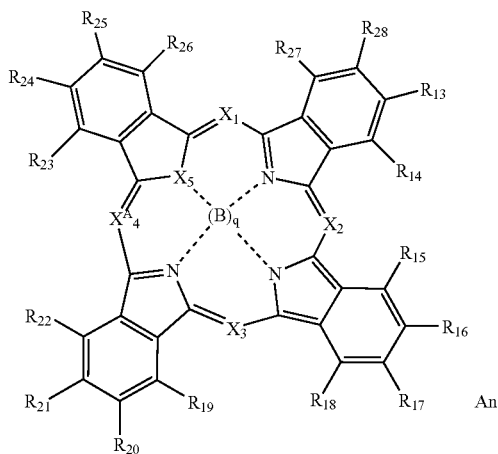

in which:
the radicals $R_{13}$ to $R_{28}$, which may be identical or different, are chosen from at least one of the following:
hydrogen;
linear or branched $C_1$-$C_{30}$ alkyl radicals; linear or branched $C_2$-$C_{30}$ alkenyl radicals;
linear or branched $C_2$-$C_{30}$ alkynyl radicals;
wherein the alkyl, alkenyl, and alkynyl radicals are optionally substituted with at least one monovalent group chosen from at least one of the following groups:
hydroxyl groups;
amino groups;
amino groups substituted with one or two linear or branched $C_1$-$C_{10}$ alkyl radicals, which may be identical or different, optionally bearing at least one group chosen from hydroxyl groups and linear or branched $C_1$-$C_{10}$ alkoxy groups;
ammonium groups substituted with one, two, or three linear or branched $C_1$-$C_{10}$ alkyl radicals, which may be identical or different, optionally bearing at least one group chosen from hydroxyl groups and linear or branched $C_1$-$C_{10}$ alkoxy groups;
hydrogenocarbonyl (—COH) groups; and
optionally substituted 5- or 6-membered heterocyclic groups, comprising at least one hetero atom, optionally bearing at least one cationic charge, wherein the heterocyclic groups is optionally fused with an aromatic nucleus;
and/or wherein the alkyl, alkenyl, and alkynyl radicals are optionally interrupted with at least one divalent group chosen from the following groups:
oxygen;
amino groups;
amino groups substituted with a linear or branched $C_1$-$C_{10}$ alkyl radical, optionally bearing at least one group chosen from hydroxyl groups and linear or branched $C_1$-$C_{10}$ alkoxy groups;
ammonium groups substituted with one or two linear or branched $C_1$-$C_{10}$ alkyl radicals, which may be identical or different, optionally bearing at least one group chosen from hydroxyl groups and linear or branched $C_1$-$C_{10}$ alkoxy groups;
carbonyl (—CO—) groups; and
optionally substituted 5- or 6-membered heterocyclic groups, comprising at least one hetero atom, optionally bearing at least one cationic charge;
optionally substituted $C_6$-$C_{30}$ aryl radicals; optionally substituted ($C_1$-$C_{30}$)alkyl($C_6$-$C_{30}$)aryl radicals; optionally substituted ($C_6$-$C_{30}$)aryl($C_1$-$C_{30}$)alkyl radicals;
hydroxyl groups;
optionally substituted linear or branched $C_1$-$C_{30}$ alkoxy radicals;
amino radicals; amino radicals bearing at least one optionally substituted linear or branched $C_1$-$C_{30}$ alkyl radical;
radicals —$SO_2$—$NH_2$, —$SO_2$NH-alkyl, and —NH—$SO_2$-alkyl, in which the alkyl radical is an optionally substituted linear or branched $C_1$-$C_{30}$ alkyl; and
optionally cationic, optionally aromatic, 5- or 6-membered heterocyclic radical, comprising at least one nitrogen atom, and optionally at least one other hetero atom, which may be identical or different, wherein the heterocyclic radical is optionally substituted;
wherein at least one of the radicals $R_{13}$ to $R_{28}$ bears at least one cationic charge;
$X_1$ to $X_4$, which may be identical or different, are chosen from nitrogen and groups —$CR_{29}$,
wherein $R_{29}$ has the same definition as $R_{13}$ to $R_{28}$;
$X_5$ is chosen from nitrogen, oxygen, and sulfur;
B is a metal or metal ion chosen from columns IA and IIA of the Periodic Table of the Elements, zinc, and silicon;

q is chosen from 0, 1, and 2, depending on the nature of the element B; and

An is at least one cosmetically acceptable anion that compensates the total cationic charge of the compound.

8. The method according to claim 7, wherein the at least one hetero atom is chosen from oxygen and nitrogen.

9. The method according to claim 7, wherein aromatic nucleus is 6-membered.

10. The method according to claim 7, wherein the metal or metal ion chosen from columns IA and IIA of the Periodic Table of the Elements is chosen from sodium, potassium, magnesium, and calcium.

11. The method according to claim 1, wherein the non-metallic cationic compound is used in the presence of at least one oxidizing agent.

12. The method according to claim 1, wherein the non-metallic cationic compound is used in the absence of an oxidizing agent.

13. The method according to claim 1, wherein the composition is applied to wet or dry keratin materials, without final rinsing of the composition.

14. The method according to claim 1, wherein the composition is applied to wet or dry keratin materials, in the presence of at least one oxidizing agent, and further comprising leaving the composition to act for a time that is sufficient to obtain the desired coloration, and then removing the composition.

15. A dye composition comprising, in a medium that is suitable for dyeing human keratin materials, at least one non-metallic or metallic cationic compound chosen from porphyrin compounds and phthalocyanin compounds comprising, as the metal element, at least one metal or metal ion chosen from columns IA and IIA of the Periodic Table of the Elements, zinc, and silicon, as direct dye for dyeing human keratin materials at least one polymer and/or at least one surfactant.

16. The dye composition according to claim 15, wherein the at least one non-metallic or metallic cationic compound chosen from porphyrin compounds and phthalocyanin compounds corresponds to formula (1) below, and the tautomeric forms thereof, bearing at least one cationic charge:

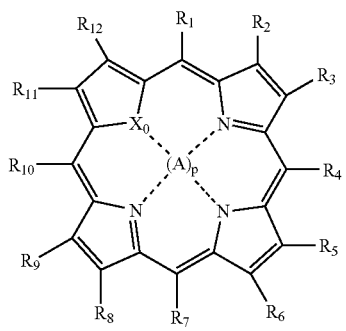

An in which:

the radicals $R_1$ to $R_{12}$, which may be identical or different, are chosen from at least one of the following:

hydrogen;

linear or branched $C_1$-$C_{30}$ alkyl radicals; linear or branched $C_2$-$C_{30}$ alkenyl radicals;

linear or branched $C_2$-$C_{30}$ alkynyl radicals;

wherein the alkyl, alkenyl, and alkynyl radicals are optionally substituted with at least one monovalent group chosen from the following groups:

hydroxyl groups;

amino groups;

amino groups substituted with one or two linear or branched $C_1$-$C_{10}$ alkyl radicals, which may be identical or different, optionally bearing at least one group chosen from hydroxyl groups and linear or branched $C_1$-$C_{10}$ alkoxy groups;

ammonium groups substituted with one, two, or three linear or branched $C_1$-$C_{10}$ alkyl radicals, which may be identical or different, optionally bearing at least one group chosen from hydroxyl groups and linear or branched $C_1$-$C_{10}$ alkoxy groups;

hydrogenocarbonyl (—COH) groups; and optionally substituted 5- or 6-membered heterocyclic groups, comprising at least one hetero atom, optionally bearing at least one cationic charge, wherein the heterocyclic groups is optionally fused with an aromatic nucleus;

and/or wherein the alkyl, alkenyl, and alkynyl radicals are optionally interrupted with at least one divalent group chosen from the following groups:

oxygen;

amino groups;

amino groups substituted with a linear or branched $C_1$-$C_{10}$ alkyl radical, optionally bearing at least one group chosen from hydroxyl groups and linear or branched $C_1$-$C_{10}$ alkoxy groups;

ammonium groups substituted with one or two linear or branched $C_1$-$C_{10}$ alkyl radicals, which may be identical or different, optionally bearing at least one group chosen from hydroxyl groups and linear or branched $C_1$-$C_{10}$ alkoxy groups;

carbonyl (—CO—) groups; and optionally substituted 5- or 6-membered heterocyclic groups, comprising at least one hetero atom, optionally bearing at least one cationic charge;

optionally substituted $C_6$-$C_{30}$ aryl radicals; optionally substituted ($C_1$-$C_{30}$)alkyl($C_6$-$C_{30}$)aryl radicals; optionally substituted ($C_6$-$C_{30}$)aryl($C_1$-$C_{30}$)alkyl radicals;

hydroxyl groups;

optionally substituted linear or branched $C_1$-$C_{30}$ alkoxy radicals;

amino radicals; amino radicals bearing at least one optionally substituted linear or branched $C_1$-$C_{30}$ alkyl radical;

radicals —SO$_2$—NH$_2$, —SO$_2$NH-alkyl, and —NH—SO$_2$-alkyl, in which the alkyl radical is an optionally substituted linear or branched $C_1$-$C_{30}$ alkyl; and optionally cationic, optionally aromatic, 5- or 6-membered heterocyclic radicals, comprising at least one nitrogen atom, and optionally at least one other hetero atom, which may be identical or different, the said heterocyclic radical being optionally substituted;

wherein at least one of the radicals $R_1$ to $R_{12}$ bears at least one cationic charge;

$X_0$ is chosen from nitrogen and oxygen;

A is a metal or metal ion chosen from columns IA and IIA of the Periodic Table of the Elements, zinc, and silicon;

p is chosen from 0, 1, and 2 depending on the nature of the element A; and

An is at least one cosmetically acceptable anion that compensates the total cationic charge of the compound.

17. The dye composition according to claim 16, wherein the at least one hetero atom is chosen from nitrogen and oxygen.

18. The dye composition according to claim 16, wherein the aromatic nucleus is 6-membered.

19. The dye composition according to claim 16, wherein the metal or metal ion chosen from columns IA and IIA of the Periodic Table of the Elements is chosen from sodium, potassium, magnesium, and calcium.

20. The dye composition according to claim 15, wherein the non-metallic or metallic cationic compound chosen from porphyrin compounds and phthalocyanin compounds corresponds to the following formula, and the tautomeric forms thereof, bearing at least one cationic charge:

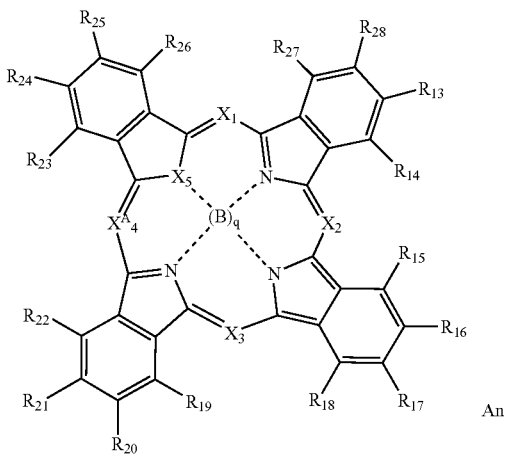

in which:
the radicals $R_{13}$ to $R_{28}$, which may be identical or different, are chosen from at least one of the following:
hydrogen;
linear or branched $C_1$-$C_{30}$ alkyl radicals; linear or branched $C_2$-$C_{30}$ alkenyl radicals;
linear or branched $C_2$-$C_{30}$ alkynyl radicals;
wherein the alkyl, alkenyl, and alkynyl radicals are optionally substituted with at least one monovalent group chosen from the following groups:
hydroxyl groups;
amino groups;
amino groups substituted with one or two linear or branched $C_1$-$C_{10}$ alkyl radicals, which may be identical or different, optionally bearing at least one group chosen from hydroxyl groups and linear or branched $C_1$-$C_{10}$ alkoxy groups;
ammonium groups substituted with one, two, or three linear or branched $C_1$-$C_{10}$ alkyl radicals, which may be identical or different, optionally bearing at least one groups chosen from hydroxyl groups and linear or branched $C_1$-$C_{10}$ alkoxy groups;
hydrogenocarbonyl (—COH) groups; and
optionally substituted 5- or 6-membered heterocyclic groups, comprising at least one hetero atom, optionally bearing at least one cationic charge, wherein the heterocyclic groups is optionally fused with an aromatic nucleus;
and/or wherein the said alkyl, alkenyl, and alkynyl radicals are optionally interrupted with at least one divalent group chosen from the following groups:
oxygen;
amino groups;
amino groups substituted with a linear or branched $C_1$-$C_{10}$ alkyl radical, optionally bearing at least one group chosen from hydroxyl groups and linear or branched $C_1$-$C_{10}$ alkoxy groups;
ammonium groups substituted with one or two linear or branched $C_1$-$C_{10}$ alkyl radicals, which may be identical or different, optionally bearing at least one group chosen from hydroxyl groups and linear or branched $C_1$-$C_{10}$ alkoxy groups;
carbonyl (—CO—) groups; and
optionally substituted 5- or 6-membered heterocyclic groups, comprising at least one hetero atom, optionally bearing at least one cationic charge;
optionally substituted $C_6$-$C_{30}$ aryl radicals; optionally substituted ($C_1$-$C_{30}$)alkyl($C_6$-$C_{30}$)aryl radicals; optionally substituted ($C_6$-$C_{30}$)aryl($C_1$-$C_{30}$)alkyl radicals;
hydroxyl groups;
optionally substituted linear or branched $C_1$-$C_{30}$ alkoxy radicals;
amino radicals; amino radicals bearing at least one optionally substituted linear or branched $C_1$-$C_{30}$ alkyl radical;
radicals —$SO_2$—$NH_2$, —$SO_2$NH-alkyl, and —NH—$SO_2$-alkyl, in which the alkyl radical is an optionally substituted linear or branched $C_1$-$C_{30}$ alkyl; and
optionally cationic, optionally aromatic, 5- or 6-membered heterocyclic radicals, comprising at least one nitrogen atom, and optionally at least one other hetero atom, which may be identical or different, wherein the heterocyclic radical is optionally substituted;
wherein at least one of the radicals $R_{13}$ to $R_{28}$ bears at least one cationic charge;
$X_1$ to $X_4$, which may be identical or different, are chosen from nitrogen and groups —$CR_{29}$,
wherein $R_{29}$ has the same definition as the abovementioned $R_{13}$ to $R_{28}$;
$X_5$ is chosen from nitrogen, oxygen, and sulfur;
B is a metal or metal ion chosen from columns IA and IIA of the Periodic Table of the Elements, zinc, and silicon;
q is chosen from 0, 1, and 2, depending on the nature of the element B; and
An is at least one cosmetically acceptable anion that compensates the total cationic charge of the compound.

21. The dye composition according to claim 20, wherein the at least one hetero atom is chosen from nitrogen and oxygen.

22. The dye composition according to claim 20, wherein the aromatic nucleus is 6-membered.

23. The dye composition according to claim 20, wherein the metal or metal ion chosen from columns IA and IIA of the Periodic Table of the Elements is chosen from sodium, potassium, magnesium, and calcium.

24. The dye composition according to claim 15, wherein the non-metallic or metallic cationic compound chosen from porphyrin compounds and phthalocyanin compounds is present in an amount ranging from 0.0005% to 20% by weight relative to the total weight of the dye composition.

25. The dye composition according to claim 15, wherein the at least one surfactant is chosen from nonionic, anionic, cationic, and amphoteric surfactants.

26. The dye composition according to claim 25, wherein the at least one surfactant is present in an amount ranging from 0.001% to 30% by weight relative to the total weight of the dye composition.

27. The dye composition according to claim 15, wherein the at least one polymer is chosen from nonionic, cationic, anionic, and amphoteric polymers.

28. The dye composition according to claim 15, wherein the at least one polymer is chosen from associative and non-associative thickening polymers.

29. The dye composition according to claim 28, wherein the at least one polymer chosen from associative and non-associative thickening polymers is present in an amount ranging from 0.01% to 10% by weight relative to the total weight of the dye composition.

30. The dye composition according to claim 29, wherein the at least one polymer chosen from associative and non-associative thickening polymers is present in an amount ranging from 0.1% to 5% by weight relative to the total weight of the dye composition.

31. The dye composition according to claim 15, wherein the at least one polymer is chosen from conditioning polymers and fixing polymers.

32. The dye composition according to claim 31, wherein the at least one polymer chosen from conditioning polymers and fixing polymer is present in an amount ranging from 0.01% to 20% by weight relative to the total weight of the dye composition.

33. The dye composition according to claim 32, wherein the at least one polymer chosen from conditioning polymers and fixing polymer is present in an amount ranging from 0.1% to 5% by weight relative to the total weight of the dye composition.

34. The dye composition according to claim 15, further comprising at least one additional direct dye other than the non-metallic cationic compound.

35. The dye composition according to claim 34, wherein the at least one additional direct dye is present in an amount ranging from 0.0005% to 12% by weight relative to the total weight of the composition.

36. The dye composition according to claim 15, further comprising at least one oxidation base, optionally combined with at least one coupler.

37. The dye composition according to claim 36, wherein the at least one oxidation base is present, for each oxidation base, in an amount ranging from 0.0005% to 12% by weight relative to the total weight of the dye composition.

38. The dye composition according to claim 36, wherein the at least one coupler is present, for each coupler, in an amount ranging from 0.0001% to 10% by weight relative to the total weight of the dye composition.

39. The dye composition according to claim 15, further comprising at least one oxidizing agent.

40. A ready-to-use composition comprising, in a medium that is suitable for dyeing human keratin materials,
at least one non-metallic or metallic cationic compound chosen from porphyrin compounds and phthalocyanin compounds comprising as the metal element, at least one metal or metal ion chosen from columns IA and IIA of the Periodic Table of the Elements, zinc, and silicon, and
at least one oxidizing agent.

41. A multi-compartment device for dyeing keratin materials, comprising at least one first compartment comprising, in a medium that is suitable for dyeing human keratin fibers,
at least one non-metallic or metallic cationic compound chosen from porphyrin compounds and phthalocyanin compounds comprising as the metal element at least one metal or metal ion chosen from columns IA and IIA of the Periodic Table of the Elements, zinc, and silicon,
optionally at least one additional direct dye, and
optionally at least one oxidation base and/or at least one coupler,
wherein these compounds are present in at least one composition, optionally combined, and
at least one second compartment with a composition comprising, in a medium that is suitable for dyeing human keratin fibers, at least one oxidizing agent.

42. A compound of the formula:

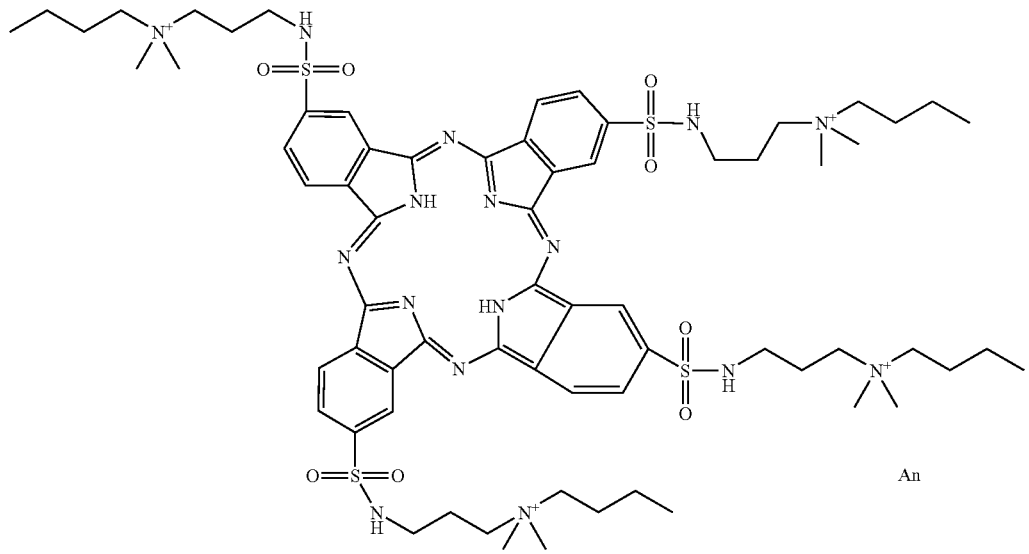

UNITED STATES PATENT AND TRADEMARK OFFICE
CERTIFICATE OF CORRECTION

PATENT NO.       : 7,429,275 B2
APPLICATION NO.  : 11/315281
DATED            : September 30, 2008
INVENTOR(S)      : Leila Hercouet et al.

It is certified that error appears in the above-identified patent and that said Letters Patent is hereby corrected as shown below:

In claim 7, column 50, line 24, "groups is" should read --groups are--.

In claim 16, column 52, line 20, "groups is" should read --groups are--.

In claim 20, column 53, line 53, "one groups" should read --one group--.

In claim 20, column 53, line 59, "groups is" should read --groups are--.

In claim 32, column 55, line 16, "fixing polymer" should read --fixing polymers--.

In claim 33, column 55, line 21, "fixing polymer" should read --fixing polymers--.

Signed and Sealed this

Seventh Day of April, 2009

JOHN DOLL
*Acting Director of the United States Patent and Trademark Office*